United States Patent
Haefele et al.

(10) Patent No.: US 10,099,012 B2
(45) Date of Patent: Oct. 16, 2018

(54) CLOSURE SYSTEM FOR AN APPLICATOR ATTACHMENT ON A CONTAINER FOR PHARMACEUTICAL PREPARATIONS, AND USE, CONTAINER WITH CLOSURE SYSTEM, SYRINGE FOR MEDICAL PURPOSES, AND METHOD OF ASSEMBLY

(71) Applicant: Boehringer Ingelheim International GMBH, Ingelheim (DE)

(72) Inventors: Friedrich Haefele, Ingelheim am Rhein (DE); Markus Hemminger, Ingelheim am Rhein (DE); Tobias Sachsse, Ingelheim am Rhein (DE); Klaus Boje, Ingelheim am Rhein (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 375 days.

(21) Appl. No.: 14/388,328

(22) PCT Filed: Mar. 19, 2013

(86) PCT No.: PCT/EP2013/055668
§ 371 (c)(1),
(2) Date: Sep. 26, 2014

(87) PCT Pub. No.: WO2013/149821
PCT Pub. Date: Oct. 10, 2013

(65) Prior Publication Data
US 2015/0165127 A1    Jun. 18, 2015

(30) Foreign Application Priority Data

Apr. 4, 2012  (DE) .................. 10 2012 006 885
Apr. 4, 2012  (DE) .................. 10 2012 006 886

(51) Int. Cl.
*A61M 5/31* (2006.01)
*B65B 7/01* (2006.01)
*B65D 43/02* (2006.01)

(52) U.S. Cl.
CPC ............. *A61M 5/3134* (2013.01); *B65B 7/01* (2013.01); *B65D 43/02* (2013.01);
(Continued)

(58) Field of Classification Search
CPC .. A61M 2005/3104; A61M 2005/3106; A61M 2005/3123; A61M 5/3134
See application file for complete search history.

(56) References Cited

U.S. PATENT DOCUMENTS 5,135,496 A    8/1992  Vetter
5,320,603 A *  6/1994  Vetter ................... A61M 5/284
                                                      604/416

(Continued)

FOREIGN PATENT DOCUMENTS

DE    4127650 C1    2/1993
DE    4434644 A1    4/1996
(Continued)

OTHER PUBLICATIONS

International Search Report for corresponding application No. PCT/EP2013/055668, dated Jul. 12, 2013.
(Continued)

*Primary Examiner* — Deanna K Hall
(74) *Attorney, Agent, or Firm* — Matthew B. Dernier, Esq.

(57) ABSTRACT

Disclosed are a closure system for an applicator attachment on a container for pharmaceutical preparations and to a use of the closure system, a syringe for medical purposes, including a container for pharmaceutical preparations and a closure system, and a method of assembling a syringe. The
(Continued)

aforementioned operate such that splash prevention and a venting function are integrated in the closure system.

22 Claims, 7 Drawing Sheets

(52) U.S. Cl.
CPC ............... *A61M 2005/3104* (2013.01); *A61M 2005/3106* (2013.01); *A61M 2005/3123* (2013.01)

(56) References Cited

U.S. PATENT DOCUMENTS

| | | |
|---|---|---|
| 5,624,402 A | 4/1997 | Imbert |
| 5,785,691 A | 7/1998 | Vetter |
| 6,280,418 B1 | 8/2001 | Reinhard et al. |
| 6,491,665 B1 | 12/2002 | Vetter et al. |
| 7,645,267 B2 | 1/2010 | Vetter |
| 2006/0129108 A1 | 6/2006 | Vetter |
| 2011/0015578 A1 | 1/2011 | Lowke |

FOREIGN PATENT DOCUMENTS

| | | |
|---|---|---|
| DE | 19537163 C1 | 1/1997 |
| DE | 102008013198 A1 | 9/2009 |
| EP | 0397951 A1 | 11/1990 |
| EP | 0749760 A2 | 12/1996 |
| EP | 1034810 A2 | 9/2000 |
| WO | 2004045681 A2 | 6/2004 |

OTHER PUBLICATIONS

International Preliminary Report on Patentability and Written Opinion for corresponding application No. PCT/EP2013/055668, dated Oct. 16, 2014.

\* cited by examiner

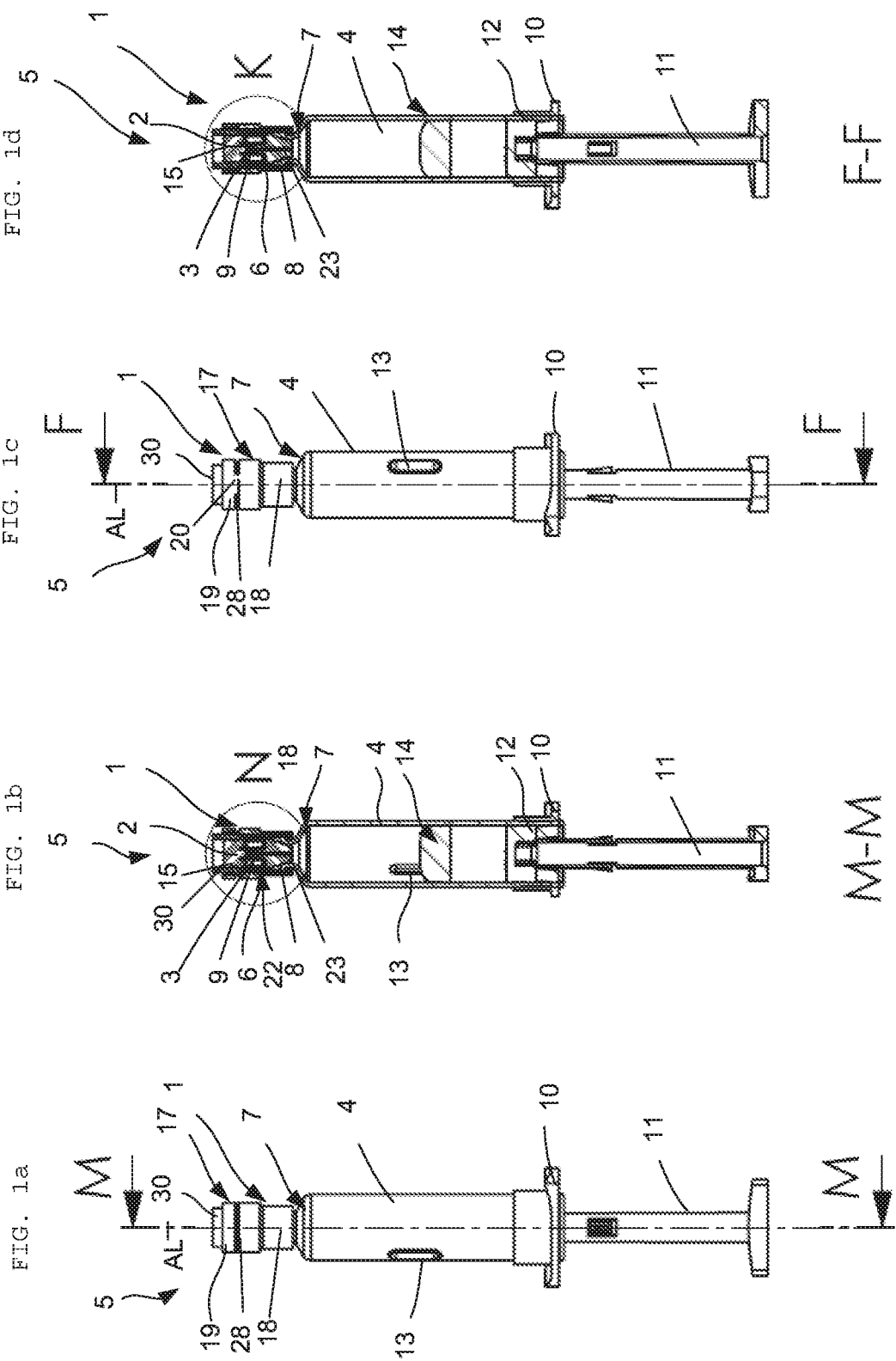

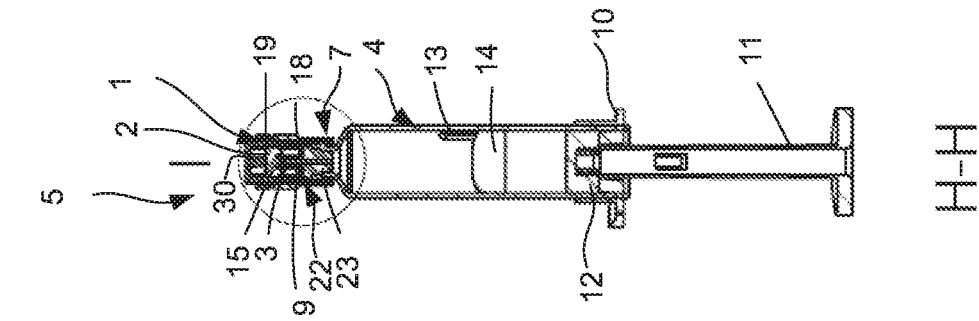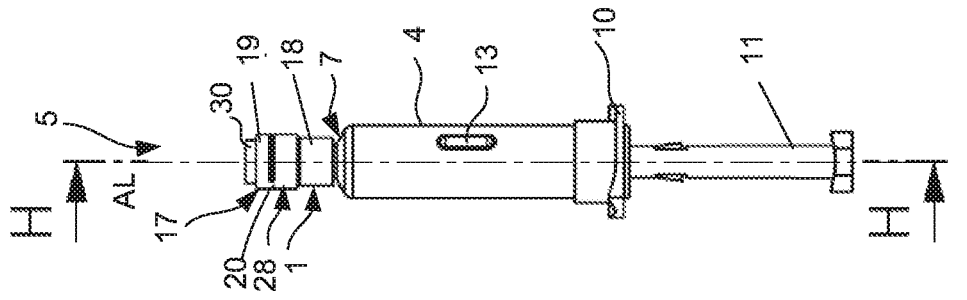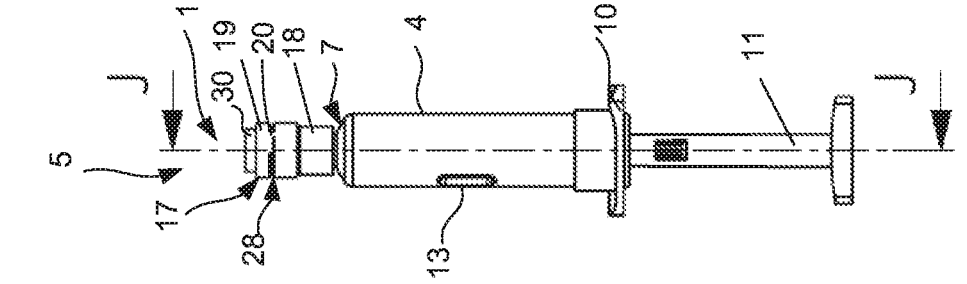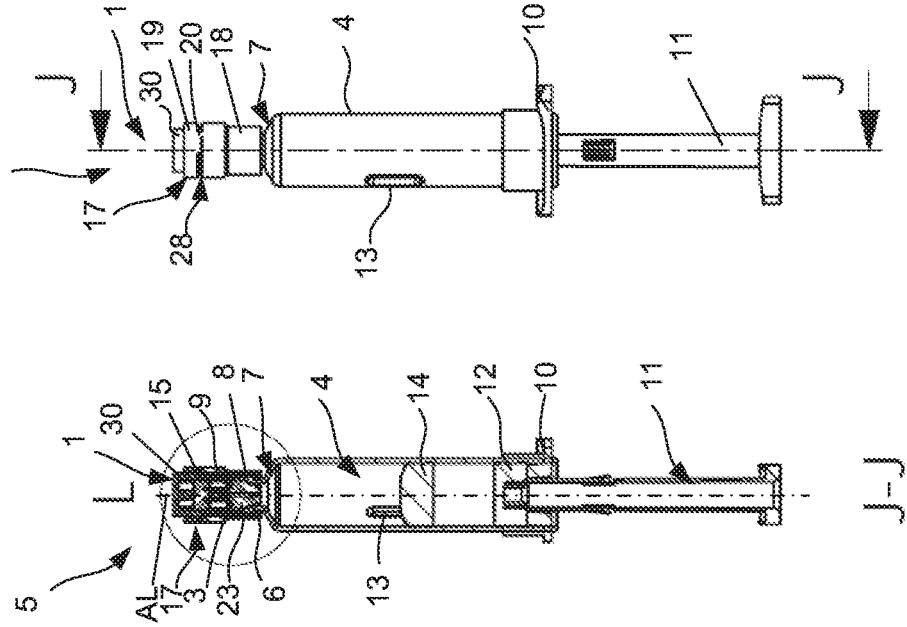

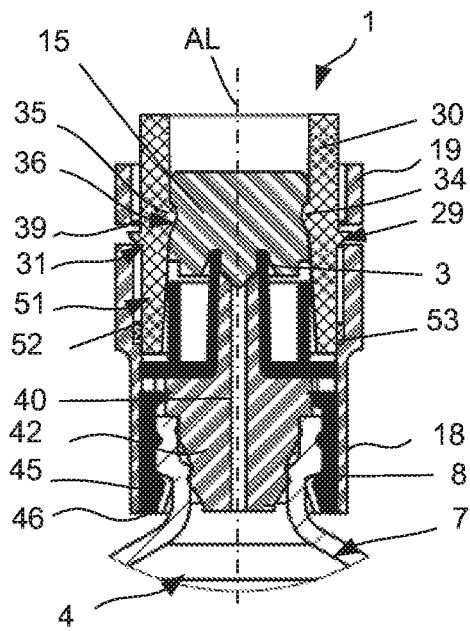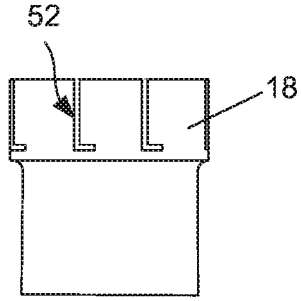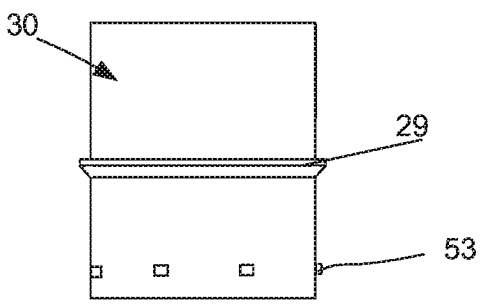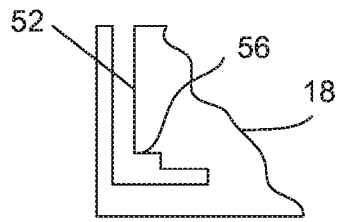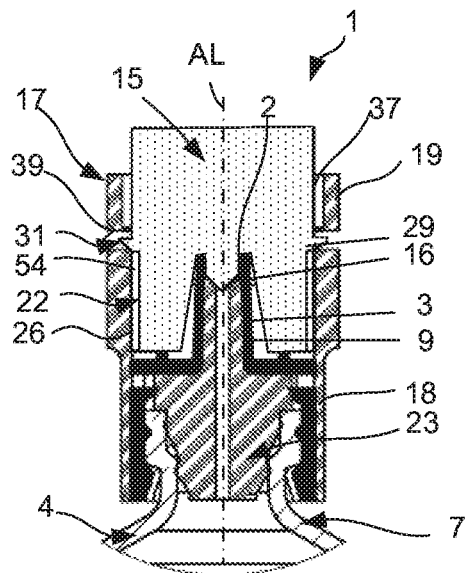

CLOSURE SYSTEM FOR AN APPLICATOR ATTACHMENT ON A CONTAINER FOR PHARMACEUTICAL PREPARATIONS, AND USE, CONTAINER WITH CLOSURE SYSTEM, SYRINGE FOR MEDICAL PURPOSES, AND METHOD OF ASSEMBLY

The invention relates to a closure system for an applicator attachment on a container for pharmaceutical preparations and to a use of the closure system. The invention also relates to a container for pharmaceutical preparations comprising a closure system. The invention also relates to a syringe for medical purposes, comprising a container and a closure system, and to a method of assembly.

A syringe for medical purposes is previously known for example from the documents EP 0 397 951 A1 and DE 195 37 163 C1. Said syringe comprises an applicator attachment which is placed onto a mouthpiece of the container, is closed by a closure element in the form of for example a tip cap until the time of use and is designed for the attachment of an applicator, for example a cannula. The applicator attachment is formed on a portion of the safety cap and via the latter is held on the mouthpiece and is sealingly connected to the container. The safety cap is non-detachably fixed to the cylindrical mouthpiece of the container by a securing ring which is pushed on and latches thereto, wherein the securing ring carries a securing cap which is securely connected thereto but is designed such that it can be separated, which securing cap encloses the applicator attachment as well as the closure element and to this end consists of a substantially hollow-cylindrical body which is at least partially closed by an end wall at an end region remote from the container. The document DE 195 37 163 C1 discloses a further development of the closure securing unit which encloses at least the end region of the applicator attachment and the closure element so as to create a tamper-proof closure on which, besides the connecting webs between the securing cap and the securing ring which form the predetermined breaking point, spacers are additionally also provided which are arranged at intervals between two adjacent web elements between the securing cap and the securing ring. The closure system characterized by the closure element, the applicator attachment and the closure securing unit allows a pressure-tight, media-tight and microbially tight closure of the container containing at least one pharmaceutical preparation for storage purposes. Only at the desired time of use is the connection between the securing cap and the securing ring destroyed, the closure element is moved out of its position in which it seals the applicator attachment and the connection to the interior of the container is opened. In order to assemble the syringe, it is necessary firstly to manufacture the individual components of the closure system on suitably designed machines, if necessary to clean said components and optionally siliconize and sterilize them, for example by autoclaving, in order then to supply these to the further production process under strict cleanroom conditions. In order to improve the procedures, there is previously known from the document EP 1 034 810 A1 a closure system in which the securing ring is separably connected to a securing cap via connecting means and the closure element is held in the securing cap with a form fit. The closure system can be handled as a fully preassembled and treated unit when assembling a syringe. However, very high demands are placed on the manufacturing precision in order to guarantee the sealing effect in the closed state of the applicator attachment.

There are pharmaceutical preparations, in particular drugs, which lose their efficacy very quickly in the liquid state. In order to be able to use these in spite of their short shelf life, special devices and methods for lyophilization have been developed. Pharmaceutical preparations which cannot be used over a long time in solution can thus be preserved by lyophilization and optionally stored under air exclusion. The dry substance is dissolved again, that is to say reconstituted, immediately prior to use. To this end, two-component systems have become known for dissolving the lyophilizate again immediately prior to use. Storage takes place in single-chamber containers with an integrated dual-chamber system or in dual-chamber containers which can be closed at an end region by the closure system known from the prior art. Since a splashing of solution is possible once the closure element has been removed at the time of venting of the container and at the time of reconstitution, for this process usually an additional cap is used to prevent splashes. The cap is difficult to fit and does not fully suppress either the risk of contamination of the surrounding environment by the solution or the risk of contamination of the solution by the surrounding environment. Furthermore, the complete sterility of the solution is threatened.

A container comprising a generic closure system according to the preamble of claim 1 is previously known from the documents DE 195 37 163 C1 and DE 41 27 650 A1. These designs permit a sterile closure while still in the lyophilizer, but there is no splash prevention upon opening.

In contrast, there are previously known from the documents U.S. Pat. No. 5,624,402 and DE 44 34 644 C2 closure systems which prevent splashes at the time of opening of the closure element but which are not suitable for closing a container, in particular a dual-chamber container, while still in the lyophilizer.

The problem addressed by the invention is that of further developing a closure system for an applicator attachment on a container for pharmaceutical preparations such that said closure system is suitable on the one hand for closing a container with a dual-chamber system, in particular a dual-chamber container, in a quick and easy manner in a lyophilizer and on the other hand for reliably ensuring the sterility during the necessary venting of the connected container at the time of the desired connection of an applicator to an applicator attachment, wherein both the risk of contamination by splashing preparation or solution and the risk of contamination of the solution are avoided. Furthermore, a tamper-proof closure is intended to prevent any wrongful opening prior to use.

The solution according to the invention is characterized by the features of claims 1, 21, 22, 24 and 25. Advantageous further developments and embodiments are portrayed in the dependent claims.

A closure system for an applicator attachment on a container for pharmaceutical preparations, said applicator attachment extending along a theoretical longitudinal axis, having a through-opening and being suitable for the connection of an applicator, said closure system comprising
  a closure element with at least one region having a sealing surface for sealing the through-opening of the applicator attachment;
  a sleeve-like connection element for force-fitting and/or form-fitting connection to the container in the end region on the applicator side;
  a closure securing unit arranged coaxial with the connection element and surrounding the latter in the circumferential direction, said closure securing unit comprising a securing ring and a securing part which is connected to the securing ring via connecting means so as to be separable with irreversible destruction of the latter, wherein the closure securing unit is designed to surround at least the end region of the applicator attachment and the closure element in the circumferential direction around the longitudinal axis over a portion of the extension in the longitudinal direction and to surround and preferably fix the sleeve-like connection element to the container in the circumferential direction by a relative movement in the longitudinal direction relative to the connection element from a first into a second assembled position, is characterized according to the invention in that the closure element is detachably connected in a force-fitting and/or form-fitting manner at least indirectly to a connection part formed by the applicator attachment or a by a functional element carrying the latter or by the securing ring. The closure element in a first functional position defined as the closed position closes the through-opening on the applicator attachment in a pressure-tight, media-tight and microbially tight manner. The form-fitting and/or force-fitting connection is arranged and designed in such a way as to be suitable for permitting, after the securing part has been separated from the securing ring, a relative movement between the components involved in the connection, in particular the closure element and the connection part, with a directional component in the direction of the longitudinal axis from the first functional position (closed position) into at least one further functional position (splash-preventing and/or venting position) while at least partially maintaining this connection, wherein in the at least one further functional position the pressure-tight, media-tight and microbially tight sealing of the through-opening on the applicator attachment by the closure element is canceled so as to form an intermediate space that is formed between the closure element, the applicator attachment and/or the connection part.

The longitudinal axis describes the orientation of the closure system and of the individual parts thereof in the longitudinal direction. In the case of an advantageous cylindrical design and a coaxial arrangement of the individual components, said longitudinal axis coincides with the central axis.

Media-tight includes the tightness in each case relative to at least one medium or a plurality of the following media or mixtures thereof: liquids, gases, solids or mixtures thereof.

An at least indirect connection between two components is understood to mean a connection which is either configured directly between two components or else is achieved indirectly, that is to say via further interposed transmission elements or components. Such an indirect connection is configured for example between a component in the form of a holding part, which carries the closure element, and a connection part. Preferably, the connection of the closure element or of a holding part holding the latter preferably takes place directly to a connection part. However, connections using a component connected to the connection part are also conceivable.

Various components of the closure system may act as the connection part. Preferably, the connection part is formed by the securing ring of the closure securing unit. The use of another functional element, for example of the applicator attachment or of a component carrying the latter or of a safety cap, is also conceivable.

The functional position of the closure element describes the position thereof, in particular the arrangement of the at least one sealing surface relative to the through-opening of the applicator attachment at least in the assembled state of the closure system on the container. In the "closed in a pressure-tight, media-tight and microbially tight manner" functional state of the applicator attachment, the functional position of the closure element corresponds to the first functional position, in which the through-opening of the applicator attachment is closed by said closure element. The second functional position may be adjustable in a fixedly defined manner, for example by a latching position or at will within the theoretically possible connection region in the direction of the longitudinal axis of the at least indirect connection between the closure element and the connection part. In the "unclosed or connection of the applicator" functional state of the applicator attachment, the closure element is fully removed therefrom.

The term "assembled position" describes the possible positions of the closure securing unit and of the individual components of the closure securing unit relative to one another in relation to the connection element for fixing to the container during the process of closing the container. At least two assembled positions are fundamentally defined, but intermediate positions are also conceivable.

The solution according to the invention offers the advantage of an easily achievable integration of the splash-preventing and venting function in a closure system that is required in any case for an applicator attachment, by using the components of the closure system, as a result of which a high concentration of functions is achieved with a small number of components. Specifically, the components of the closure system which delimit the intermediate space in the second functional position of the closure element simultaneously form the splash-preventing means. There is no need for a splash-preventing cap which is additionally to be provided and which is fitted after removal of the closure element, and the disadvantages associated therewith are avoided. Furthermore, simply on account of the design of the resulting intermediate space in the second functional position, a pressure reduction in the intermediate space can take place even when the connection is designed to be tight. The design according to the invention is also suitable in a particularly advantageous manner for closing a container for pharmaceutical preparations having a dual-chamber system, in particular a dual-chamber container, in the lyophilizer since, due to the position of the closure element in the closure system, which is already fixedly defined by the connection between the closure element and the connection part, the coaxial arrangement of the closure element, the closure securing unit and the connection element relative to one another and the possibility of the relative movement between the closure securing unit and the connection element in the longitudinal direction between a first and a second assembled position, only a force in the longitudinal direction is required for closing purposes, which can be generated within the lyophilizer.

In one advantageous further development, venting means are provided which are arranged and designed in such a way as to be suitable for connecting the through-opening on the applicator attachment to the surrounding environment at least in the second functional position of the closure element. As a result, a complete pressure equalization with the surrounding environment can take place without any medium escaping from the connected container. According to one particularly advantageous design, the venting means are integrated at least partially in the at least indirect connection between the closure element and the connection part. The venting can thus be adjusted in a targeted manner depending on the arrangement and design of the venting means.

To this end, the venting means may in a first design be formed at least partially by the connecting means of the at least indirect connection between the closure element and the connection part and/or in a further second design may comprise at least one separate venting channel. Both designs can also be combined with one another.

In the design of the closure system free of components with an integrated venting channel, the venting position is achieved solely by at least partially canceling the at least indirect connection between the closure element and the connection part by a relative movement of these relative to one another into the suitable venting position.

In a design with at least one venting channel, this channel is/these channels are incorporated either in the connecting means on one of the components to be connected to one another, for example by providing open-edged cutouts, or by forming regions free of connecting means on at least one of the components to be connected to one another.

In all of the aforementioned designs, the splash-preventing and/or venting position can be configured such as to be perceptible to the user, preferably visually or else by touch, for example via suitable markings which are arranged and configured on the closure element and the connection part in such a way as to be suitable for assuming a predefined position relative to one another when the second functional position (splash-preventing and/or venting position) is reached. Preferably, markings are selected which in the second functional position assume a position opposite one another or an overlapping position.

An at least indirect connection between the closure element and the connection part can take place according to a first design indirectly, that is to say via at least one further component connected to the closure element, or according to a second design directly. In the first design, the at least indirect connection between the closure element and the connection part is formed indirectly by a connection between a holding part, which surrounds the closure element as seen at least in the circumferential direction around the longitudinal axis and is connected thereto, and the connection part, and the connection between the closure element and the holding part is designed as one of the connections mentioned below or as a combination of these:
  force-fitting connection
  form-fitting connection
  material bond.

The form fit which acts in the direction of the longitudinal axis and at least counter to the detachment movement direction of the closure element and which is formed at least indirectly between the closure element and the securing part is then formed between the holding part and the securing part. This solution offers the advantage of a geometrically simple and compact design of the closure element as a solid element. The choice of material for the connection part, particularly in the connection region, is not limited by the materials of the closure element that are permissible for the sealing function. Instead, inexpensive materials and simple production methods may be used for the holding part and the connection part. The integration of the closure element in the holding part furthermore offers the advantage of forming a suitably large handling region in the longitudinal direction for opening the closure system. Specially shaped and/or formed gripping regions may be provided therein, in particular may be incorporated therein.

A force-fitting connection between the closure element and the holding part can be achieved for example by a press-fit connection. In this case, the closure element is designed to be oversized in the circumferential direction relative to the inner circumference of the holding part which holds it. The press-fit connection is preferably designed in such a way that the forces necessary to maintain the connection in the "closed" functional position can be absorbed thereby. In one advantageous further development of this connection variant, the holding part is designed to be at least partially closed in the end region directed away from the applicator attachment in the installed position or is designed to form a bearing surface, oriented counter to the detachment movement direction in the longitudinal direction, for the closure element so as to generate a pretensioning force which is exerted on the closure element at the time of establishing the connection between the holding part and the connection part, as a result of which the closure element is securely held in the holding part. In the first-mentioned case, the holding part may be designed to be at least partially closed at one end or may be designed as a cap. In the second case, a protrusion directed away from the holding part may be formed on the inner circumference of the closed end region of the holding part, so as to form a bearing surface.

In a further variant, the closure element is connected to the holding part in a form-fitting manner. The connection may be produced for example via a latching connection. The form-fitting means, in particular latching means, may in this case extend either over a portion in the circumferential direction around the longitudinal axis or else preferably entirely, as a result of which a uniform force distribution can be achieved.

In a second design, the closure element is connected directly to the connection part.

In order to be able to rule out a multiple opening and closing of the applicator attachment, an irreversible separable connection between the securing ring and the securing part is provided. This so-called tamper-proof closure is achieved in a first variant by the function concentration of the release function and moving into the second functional position. The closure element or the holding part carrying the latter is fixed relative to the securing part via a form fit formed at least indirectly between the closure element and the securing part, which form fit acts in the direction of the longitudinal axis and in particular is oriented at least counter to the detachment movement direction of the closure element. This form fit is preferably arranged in the connection region between the securing part and the securing ring, as a result of which the form fit is necessarily also canceled at the time of canceling the connection between the securing part and the securing ring. The release and the setting of the second functional position are thus permanently coupled, as a result of which it is possible to omit one handling step when it is desired to connect an applicator. This design is characterized by a high concentration of functions with a minimal number of components.

In order to achieve the permanent coupling between the separation of the connection between the securing ring and the securing part and the release of the form fit between the closure element/holding part and the securing part, which form fit acts at least in the longitudinal direction counter to the detachment direction of the closure element, components of the securing part that is to be separated are used to establish the form fit.

The form fit may in this case be arranged directly in the connection region between the securing ring and the securing part or offset in relation thereto.

In one particularly advantageous design, the securing part and the securing ring may be connected to one another via at least one connecting means formed in the longitudinal direction, for example a web having a cross section that does or does not vary in the longitudinal direction, wherein the securing part has a surface which faces toward the securing ring and is spaced apart therefrom, which surface in the first functional position of the closure element acts as a stop surface in the longitudinal direction for at least one elastic securing protrusion which is at least in the shape of a ring segment and which is formed on the closure element or on the holding part so as to be arranged around the latter in the circumferential direction. In this case, one or more such securing protrusions may be provided, which nevertheless alone or together must extend over a minimum angle range in the circumferential direction around the closure element or the holding part.

In a second variant, the tamper-proof closure is formed by connecting webs between the securing part and the securing ring.

Preferably, the at least indirect connection which permits a relative movement between the closure element or holding part and the connection part is designed at least over a portion with a form-fitting and/or force-fitting connection acting in the direction of the longitudinal axis counter to the detachment movement direction of the closure element. By virtue of the force-fitting and/or form-fitting portion of the connection region that is formed counter to the detachment movement direction, an automatic displacement of the components involved in the connection so as to cancel the seal is reliably ruled out, and the closure element is held against the applicator attachment with a basic pressing force via the connection. Depending on the type of connection that is selected, this feature is already inherent in the connection, for example in the case of a screw connection in which, in the event of static friction, no relative movement takes place between the thread turns of components that are to be connected to one another.

Several possibilities exist for the design of the connection which permits a relative movement between the closure element or holding part and the connection part. What is common to all of these possibilities is that the connection, during the relative movement, permits within the latter a movement at least of one of the components in the direction of the longitudinal axis. The relative movement may be movements in just one direction or a superposed movement, for example a rotation in the circumferential direction with simultaneous movement in the longitudinal direction. Furthermore, one component may be invariable in its position relative to a reference component or a reference surface and the other component may be movable relative thereto. The movement of both connected components relative to one another is also conceivable.

In a first solution approach, force-fitting connections are used for the connection which permits the relative movement, such as for example screw connections. In a second solution approach, form-fitting connections can be used. A third solution approach comprises a combined connection system consisting of both of the aforementioned connection types.

In one advantageous variant according to the first solution approach, the connection which permits a relative movement between the closure element or holding part and the connection element with a directional component in the direction of the longitudinal axis is formed by a screw connection, comprising a portion with an internal thread on one of the components to be connected to one another—closure element/holding part carrying the latter or connection part—and a portion with an external thread on the respective other of the components to be connected to one another—connection part or closure element/holding part carrying the latter.

In one advantageous further development of this variant of the first solution approach, either no venting channel or at least one venting channel is provided in the screw connection, which venting channel runs with at least a main directional component parallel to the longitudinal axis. The advantage of the integrated venting channel lies in the easy production either at the time of creating the thread or during the subsequent incorporation therein. In the solution with at least one venting channel, this channel is/these channels are either incorporated in the thread, for example by providing open-edged cutouts on the thread turns at least on one of the components to be connected, or is formed by interrupting the thread turns so as to form thread-free regions on at least one of the components to be connected to one another—closure element/holding part or connection part—wherein the thread-free regions are arranged and dimensioned in such a way that the single threaded region arranged between two thread-free regions encompasses an angle range which, summed over the threaded regions, ensures a trouble-free functionality of the screw connection.

The venting channel is advantageous produced by interrupting the thread on one of the two components, or on both, for example by providing thread turn segments in the circumferential direction only on the appropriate portion forming the inner or outer circumference. Such an advantageous summed angle range is in each case inclusively between 5° and 90°, preferably 8° and 60°, particularly preferably 10° and 45°, relative to the full circumference 360°. The claimed angle range ensures a secure engagement of the components to be connected to one another and the functioning of the connection.

In one advantageous further development, the functional position (splash-preventing and/or venting position) between the closure element and the applicator attachment is achieved as a function of the geometry and dimensioning of the thread. In order to achieve this, for example the thread pitch and the thickness of the thread turns can be adapted and/or a tapering of a thread turn or a widening of the corresponding thread turn at the end in the longitudinal direction can be implemented.

In one variant according to the second solution approach, the connection which permits a relative movement between the closure element or holding part and the connection part with a directional component in the direction of the longitudinal axis is formed by protrusions which are arranged on one of the components to be connected—closure element/holding part or connection part—and which point in the direction of the other component, which protrusions can be introduced into open-edged cutouts which run in the direction of the longitudinal axis on the respective other of the components to be connected to one another—connection part or closure element/holding part carrying the latter. The cutouts running in the direction of the longitudinal axis open in each case in a portion oriented in the circumferential direction, which permits a form-fit counter to the direction of the longitudinal axis.

The protrusions may be designed in various ways. Circular, oval or polygonal cross-sectional geometries are conceivable with regard to the cross-section engaging in the slots.

Depending on the materials selected for the connection part or the closure element or a holding part carrying the latter, the protrusions and the cutouts may be integrally formed therewith at the time of manufacture or may be connected thereto subsequently.

According to one particularly advantageous design, the form-fitting connection is configured in such a way as to form at least one latching position within the theoretical connection region, but outside the portion defining the first functional position, in which a form fit between the closure element and the connection part counter to the direction of the longitudinal axis is likewise enabled. To this end, the latching position is arranged on at least one of the components between the portions of the connecting means characterizing the first functional position when connected and the separation region of the other component. In the simplest case, sub-cutouts forming special latching regions are provided for this purpose in the cutouts, which sub-cutouts enable a form fit between the protrusions on the closure element or the component carrying the latter and the cutouts on the connection part, said form fit limiting the mobility of the closure element or of the holding part in the longitudinal direction.

An applicator attachment may be understood to mean a functional element or a portion of a functional element which is designed and arranged so as to be suitable for being connected to an applicator, such as a hollow needle or injection needle, a tube for a butterfly cannula or the like. To this end, the applicator attachment may have suitable means for coupling it to the applicator in a force-fitting and/or form-fitting manner, which means can be operatively connected to complementary means on the respective applicator.

The applicator attachment is hollow-cylindrical and has at least one conical portion. It may be designed as an integral component with another functional element or with the container or as a separate component without any further function.

According to a first basic design for the applicator attachment, the latter is formed by a region integrally formed on the container and the securing ring is fastened to the container in the circumferential direction and in the direction of the longitudinal axis directly or via a retaining ring which surrounds the applicator attachment in the circumferential direction.

In a second basic design, the applicator attachment is formed by a separate element or is integrally formed on a functional element which is connected at least indirectly to the container in a form-fitting and/or force-fitting manner.

The closure system comprises a closing stopper which can be inserted into an end opening on the container, has a through-opening for connecting between the container interior and the surrounding environment and has an outer circumferential surface which runs in the circumferential direction relative to the longitudinal axis and which forms over a portion a sealing surface for bearing against a portion of the inner circumference of the container in the region of the end opening. The closing stopper is fixed to the container in a force-fitting and/or form-fitting manner via a safety cap and the applicator attachment is formed by at least a portion of the safety cap or a portion on the closing stopper that extends through the safety cap. In one advantageous design, the connection element is in this case formed integrally with the safety cap.

In an alternative design, it is also conceivable that the applicator attachment is formed by or on the closing stopper and the closing stopper is connected at least indirectly to the container in a force-fitting and/or form-fitting manner. Means for fixing the securing ring in the circumferential direction around the longitudinal axis and in the direction of the longitudinal axis are provided on the closing stopper and/or on the container.

With particular advantage, the closure system is preassembled as a unit, is cleaned if necessary and can be stored in a sterile package and can be assigned as a unit to an applicator attachment for closure purposes.

The cleaning and optional sterilization of the individual components may take place individually or else for the entire preassembled unit.

According to one particularly advantageous further development, the preassembled unit also includes the applicator attachment, wherein the unit need only be connected to the container, in particular need only be pushed onto the end region that is to be closed.

In one particularly advantageous further development, the fixing of the connection element to the container is achieved by tensioning it relative to the container. In the simplest case, this may take place by means of an additionally provided tensioning ring which in the second assembled position surrounds the securing ring of the closure securing device in the circumferential direction in the extension region of the connection element and tensions the latter relative to the container. The necessary pressure for fixing, in particular tensioning, the connection element relative to the container thus need no longer be applied solely via the container-side end region of the securing ring, so that the surface area necessary for this can be kept small, which leads to a reduction in the necessary size of the securing ring and of the connection area on the connection element, resulting in a reduction in the size of the closure system in comparison to the design according to the invention without a tensioning ring.

One particularly advantageous use of a closure system according to any of claims 1 to 20 lies in using it to close a container which holds at least one pharmaceutical preparation, in particular a dual-chamber container, in order to ensure a sterile closure while still in the lyophilizer and further to allow an easy and reliable splash prevention and venting at the time of detachment of the closure element.

The container according to the invention for holding pharmaceutical preparations comprises an applicator attachment which is formed thereon or can be attached thereto and which has a closure system according to any of claims 1 to 20. With particular advantage, said container is designed as a dual-chamber container with a mouthpiece for forming the opening and for the connection of the applicator attachment, wherein the closure system can be assigned to the container, with positioning of the closure securing unit relative to the connection element, before it is introduced into the lyophilizer and in the lyophilizer the lyophilization can take place and thereafter a sterile closure while still within the lyophilizer.

To make the container and the closure system suitable for lyophilization, said container is designed as a dual-chamber container with a mouthpiece for forming the opening and for the connection of the applicator attachment, wherein the mouthpiece comprises at least two means, configured in a manner complementary to the means on the connection element, for establishing a force and/or form fit, said means being offset relative to one another in the longitudinal direction in order to keep the connection element in a first position relative to the container in the first assembled position of the closure system and in order to fix the connection element in a second position relative to the container in the second assembled position of the closure system.

With particular advantage, the container comprising such a closure system is used as a syringe for medical purposes. The splashing of solution which is possible in the prior art at the time of venting and during the reconstitution is reliably suppressed.

A method according to the invention for assembling a container with such a closure system, in particular such a syringe, is characterized by the following method steps:

preassembling the closure system consisting of at least one closure element and the closure securing unit so as to form a unit;

sterilizing and optionally if necessary cleaning the closure system;

assigning it to a container and closing an end region of a container holding pharmaceutical products.

In one particularly advantageous further development, an applicator attachment is also preassembled with the unit.

By way of example, the complete closure system can first be placed onto the container, in particular a dual-chamber container of a syringe, in a freeze-drying position and after the freeze-drying process the syringe can be completely closed by bringing together the freeze-drying plates (application of force to the closure system).

The closing of the container within a lyophilizer takes place by means of the following steps:

assigning the closure system to the container with the closure securing unit in a first assembled position relative to the connection element prior to the lyophilization (can also take place outside the lyophilizer), and displacing the closure securing unit into a second assembled position relative to the connection element, thereby fixing it to the container after the lyophilization.

In one particularly advantageous design, in the first assembled position the connection element is arranged in a first position on the end region of the container having the opening, so as to surround said container in the circumferential direction, and the closure securing unit and the closure element coupled thereto are positioned, as seen in the longitudinal direction, relative to the connection element in a position free from a sealing of the applicator attachment. The closing of the container during or after a lyophilization takes place by bringing the closure system into a second assembled position via a relative movement at least of individual components of the closure system relative to one another and/or relative to the end region containing the opening, in particular by displacing the closure securing unit and the closure element relative to the connection element in the longitudinal direction so as to sealingly close the applicator attachment and by displacing the connection element on the end region of the container so as to fix the closure system to the container after the lyophilization in a second position.

The materials for the closure element and the closing stopper are not particularly limited. Preferably an elastic, flexible material is used. Examples of this include rubber, such as natural or synthetic rubber, plastics, such as elastomers, thermoplasts, thermoplastic elastomers. Use is preferably made of rubber formulations which are permeable to vapor and/or to ethylene oxide, such as for example bromobutyls, polyisoprenes and mixtures thereof.

The material may also be provided with a coating, as a result of which for example a barrier to leachables can be created.

The container is designed as a single-chamber or multi-chamber container, in particular as a dual-chamber container which comprises a cylindrical body. This is a substantially elongate and hollow body with two open ends, which is preferably of one-piece design, that is to say has been produced in one piece, and, when designed as a dual-chamber container, is divided into chambers by separating stoppers (central and end stoppers). The material of which the cylindrical body is made or which the cylindrical body contains is not particularly limited. The container may be made from plastics or glass. Glass is widely used on account of its transparency and compatibility with many pharmaceutical formulations. The cylindrical body therefore preferably consists of glass or contains glass since this results in the least impairment to the components contained therein and the body is preferably transparent. For particular requirements, however, other materials are also suitable, such as specific plastics or the like. The pharmaceutical safety plays a particular role here, since the desire is for there to be as little interaction as possible with the medium contained therein.

Preferably, the cylindrical body has the same diameter along the entire length.

In the present invention, the term "shape" or "contour" is intended to refer to the external shape or geometry. The term "dimension" is intended to refer to the physical dimensions, that is to say the size ratios.

The solution according to the invention will be explained below with reference to figures.

Specifically, in the figures:

FIGS. 1a to 1d show, in a schematic simplified diagram, the basic structure and the basic function of a closure system according to the invention in a first variant of a first design for an applicator attachment having a through-opening and being in the form of a separate functional element for coupling to a container, based on the example of a syringe;

FIGS. 2a to 2d show, in a schematic simplified diagram, the basic structure and the basic function of a closure system according to the invention in a second variant of a first design for an applicator attachment having a through-opening and being in the form of a separate functional element for coupling to a container, based on the example of a syringe;

FIG. 3b shows a section K-K from FIG. 3a;

FIG. 5a shows by way of example, based on a view similar to FIG. 1e, a further design of a connection which permits a relative movement, as a form-fitting connection between the closure element or the holding part carrying the latter and the connection part;

FIG. 5b shows the connecting means on the securing ring for the connection which permits a relative movement;

FIG. 5c shows the connecting means on the holding part for the connection which permits a relative movement;

Figure 7:
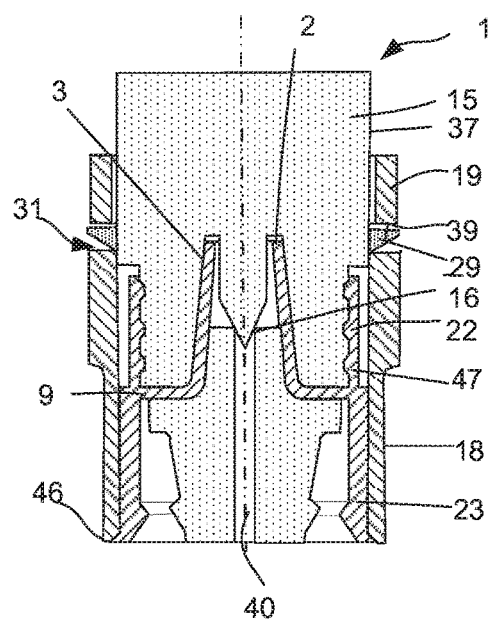
Figure 8A:
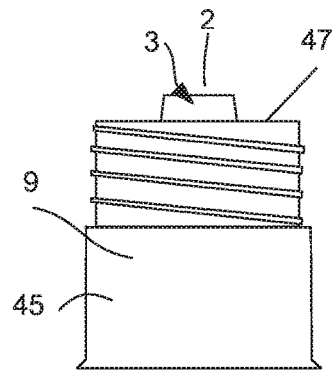
Figure 8B:
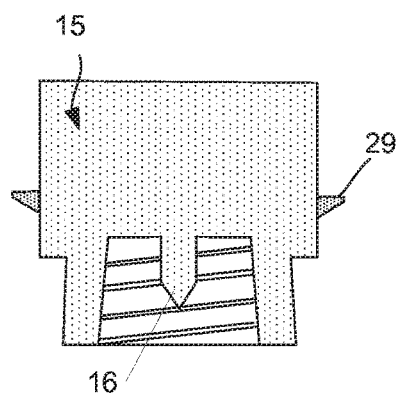
Figure 9A:
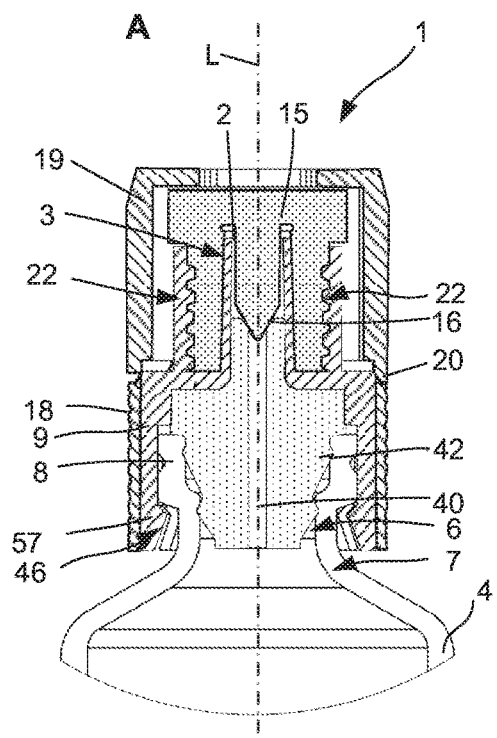
Figure 9B:
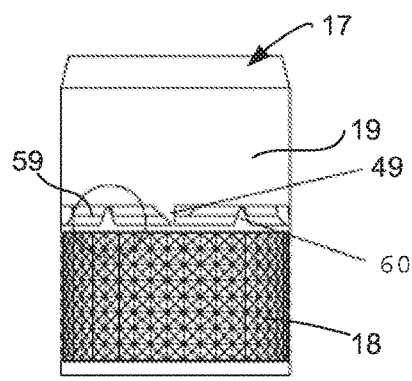
Figure 10:
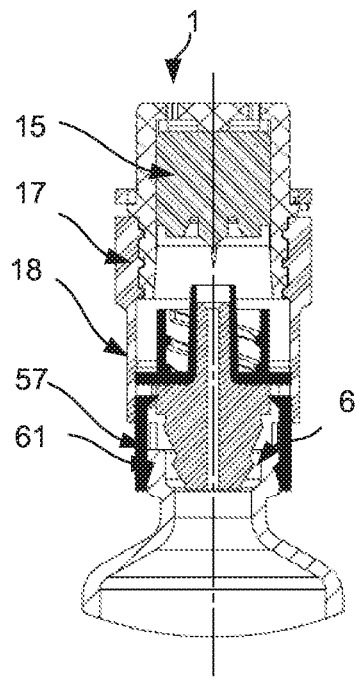
Figure 11A:
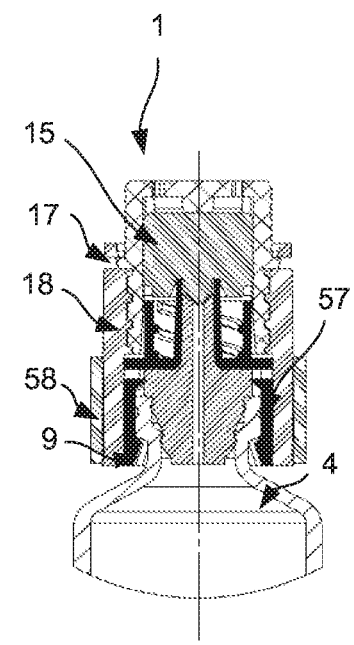
Figure 11B:
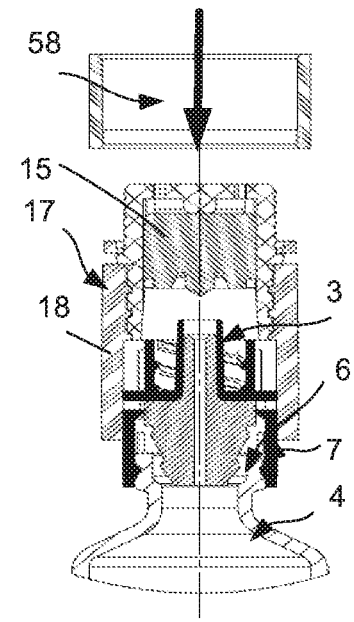
Figure 12A:
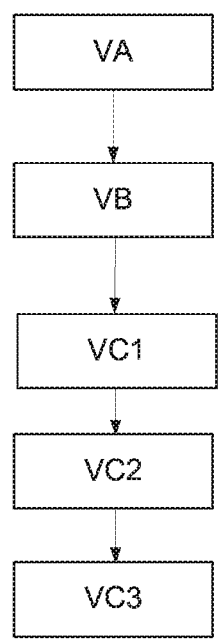
Figure 12B:
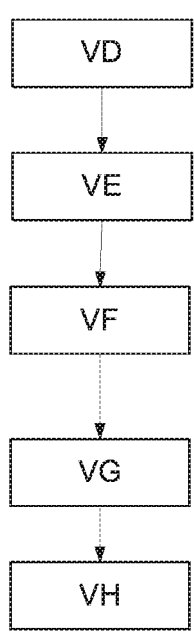

FIGS. 5d1 and 5d2 show possible embodiments of the recess with the latching position;

FIG. 6 shows a closure system according to the invention in a second design with a direct connection between the closure element and the connection part, in particular the securing ring, in an axial section;

FIG. 7 shows a closure system according to the invention in a second design with a direct connection between the closure element and the connection part, here by way of example in the form of a safety cap, in an axial section;

FIGS. 8a and 8b show, based on the design of the safety cap and the closure element, an alternative design of the closure system shown in FIG. 7;

FIGS. 9a and 9b show, based on a sectional view and a view from the right, a further design of a closure system according to the invention;

FIG. 10 shows by way of example, based on a design of a closure system according to FIGS. 2a to 2f, the positioning of the individual components relative to one another and relative to the container prior to the closing in the lyophilizer;

FIG. 11a shows by way of example one particularly advantageous further development of a closure system on a container with a tensioning ring;

FIG. 11b shows a design according to FIG. 11a in a first assembled position;

FIG. 12a shows in a schematic simplified diagram the sequence of a method for producing a syringe;

FIG. 12b shows in a schematic simplified diagram the sequence of a method at the time of opening the closure system.

Figure 13A:
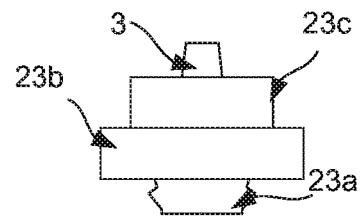
Figure 13B:
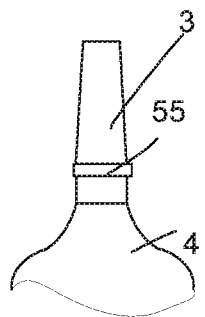

FIG. 13a shows an alternative design of the applicator attachment on the closing stopper;

FIG. 13b shows an alternative design of the applicator attachment on the container.

In the parts, identical parts have the same reference signs.

Figure 1E:
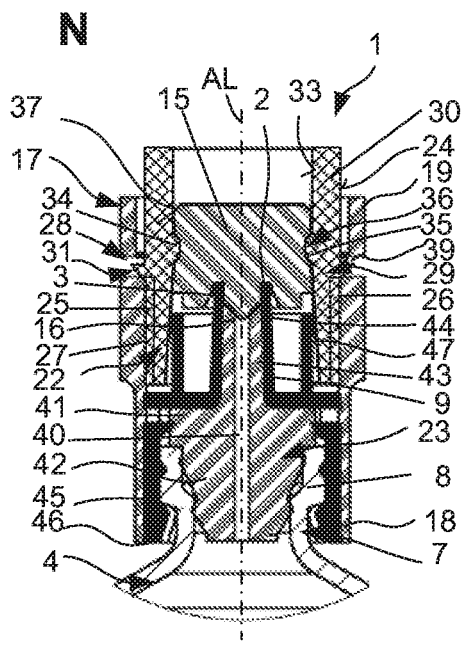
FIG. 1e shows a detail N in a view M-M from FIG. 1b.

FIGS. 1a to 1f show an embodiment of a closure system 1 according to the invention in a first variant of a first design for an applicator attachment 3 having a through-opening 2 and being in the form of a separate functional element for coupling to a container 4 which in one advantageous application is designed as a dual-chamber container for use as a syringe. FIGS. 1a and 1c show a syringe after lyophilization in the closed state of the container 4, in two different views. FIG. 1b shows a section M-M according to FIG. 1a, and FIG. 1d shows a section F-F according to FIG. 1c. The closure system 1 is shown in FIGS. 1a to 1f in its first functional position, that is to say the closed position, in which the container 4 is sealingly closed.

The separate functional element forming the applicator attachment 3 is designed as a safety cap 9 and, besides being designed as an applicator attachment 3, serves to fix in position a closing stopper 23, which closes the opening of a container 4, in the direction of a longitudinal axis AL of the closure system 1 which in the closed state of the container 4 coincides with the longitudinal axis of the container 4. In this advantageous design, the safety cap 9 is moreover formed integrally with a connection element 57 connected to the container 4, that is to say forms said connection element in a portion. The connection of the connection part 57 to the container 4 can take place in a force-fitting and/or form-fitting manner.

Figure 1F:
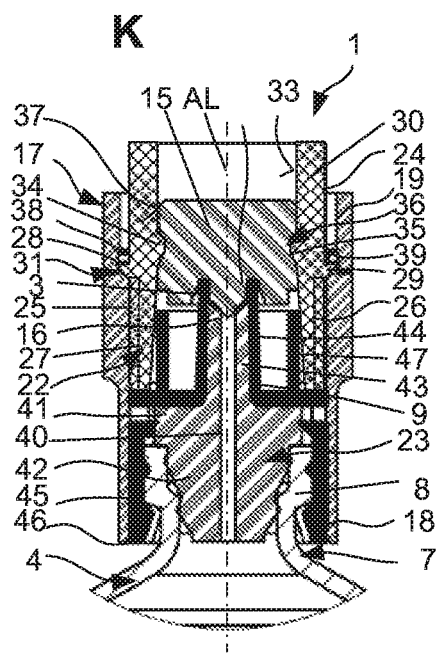
FIG. 1f shows a detail K in a view F-F from FIG. 1d.

In order to characterize the directional details, reference is made to a theoretical longitudinal axis AL which is oriented in the longitudinal direction and corresponds to the central axis of the components in the installed position. In the direction of the longitudinal axis AL means here in the longitudinal direction, and in the circumferential direction means around said longitudinal axis. FIGS. 1e and 1f each show the closure system 1 with the applicator attachment 3 in section according to details N and K in FIGS. 1b and 1d.

The container 4 is cylindrical and describes a cavity arranged around a longitudinal axis AL, wherein the cross section of the cavity is preferably circular or oval over at least a considerable portion of the extension of the container 1 in the direction of the longitudinal axis AL. The container 4 serves to hold and store one or more pharmaceutical products, which may exist as a pharmaceutical preparation in pure form or in a mixture and which can be dispensed from the container 4 through an opening 6 in an end region 7 thereof via the applicator attachment 3. The applicator attachment 3 is fixed to the container 4 at least indirectly, but preferably directly. The connection takes place in a form-fitting and/or force-fitting manner. At least indirectly means directly or via further interposed elements and components.

The container 4 has in a first end region 7 a mouthpiece 8 for forming the opening 6 and for the connection of the applicator attachment 3. The closure system 1 for closing the applicator attachment 3 is arranged and designed in such a way as to be suitable in the closed state in a first functional state (closed), which is shown in FIGS. 1a to 1f, for closing in a completely pressure-tight, media-tight and microbially tight manner the through-opening 2 of the applicator attachment 3, which through-opening is connected to the interior of the container 4, and thus the container 4 in the end region 7, and in a further functional state (open) for making it possible to remove or dispense the preparation from the container 4. When the arrangement consisting of container 4 and applicator attachment 3 is designed as a syringe 5, said syringe has a finger support 10 as well as at least one stopper 12 which can be actuated by a piston 11 that is guided in the direction of the longitudinal axis AL through at least a portion of the interior enclosed by the container 4. The latter comprises a bypass 13 as well as a further stopper 14 which, prior to use of the container 4, keeps separate two preparations and/or solutions, for example keeps a pharmaceutical preparation introduced in lyophilized form or lyophilized in the container separate from a solvent which, immediately prior to use of the syringe 5, is transferred via the bypass 13 into the chamber arranged upstream of the mouthpiece 8. In order to ensure the aforementioned functions—pressure-tight, media-tight and microbially tight closure of the opening 2 of the applicator attachment 3, removal of a pharmaceutical preparation via the through-opening 2 and coupling to an applicator for applying the pharmaceutical preparation—the closure system 1 is preferably configured in multiple parts. Preferably, the individual components are configured cylindrically around the longitudinal axis AL.

The closure system 1 comprises at least one closure element 15 which is assigned to the through-opening 2 of the applicator attachment 3, has at least one sealing surface 16 for sealing said through-opening and can be removed in order to connect the applicator to the applicator attachment 3. According to a first variant of the first design, the closure element 15 is held with a form fit in a holding part 30. The closure element is also known as a tip cap.

In order to ensure the cleanliness and sterility up until the time of actual use, a closure securing unit 17 is provided. The closure securing unit 17 surrounds in the circumferential direction the closure element 15 and at least the free end region of the applicator attachment 3, that is to say the end region directed away from the container 4, over a portion of the extension in the direction of the longitudinal axis AL and comprises a securing ring 18 which surrounds the applicator attachment 3 in the circumferential direction over a portion of its extension in the longitudinal direction and which is fixed thereto and/or to the container 4 at least indirectly. In addition, in one particularly advantageous embodiment, in order to ensure the tamper-proof closure, a securing part 19 is provided which is connected to the securing ring 18 via connecting means 20 in such a way as to be separable therefrom only by destroying said connecting means, the securing part being designed to extend in an annular manner around the closure element, preferably so as to form a gap in the radial direction relative to the longitudinal axis AL. A form fit 31 which acts in the direction of the longitudinal axis is provided at least indirectly between the closure element 15 and the securing part 19. In the case shown, the form fit 31 is achieved via the holding part 30 which holds the closure element 15.

The closure securing unit 17 is fastened to the container 2 in a force-fitting and/or form-fitting manner via the connection element 57. The connection element 57 is designed in the manner of a sleeve and engages around the opening region of the container 4. The connection between the connection element and the container 4 takes place in a force-fitting and/or form-fitting manner. Preferably, in its end region pointing toward the container, the connection element 57 is formed with web-like latching elements which, when the securing ring 18 engages around the connection element 57, are fixed relative to the container 4, in particular engage in cutouts and undercuts provided for this purpose.

Figure 1G:
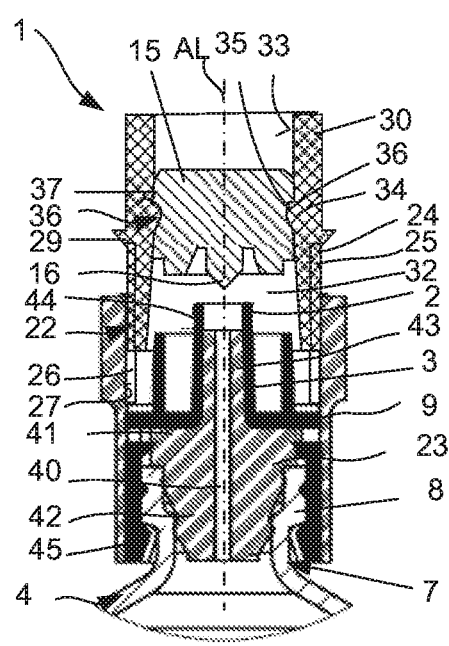
FIG. 1g shows in a view similar to FIG. 1e the closure system in the second functional position of the closure element.
Figure 1H:
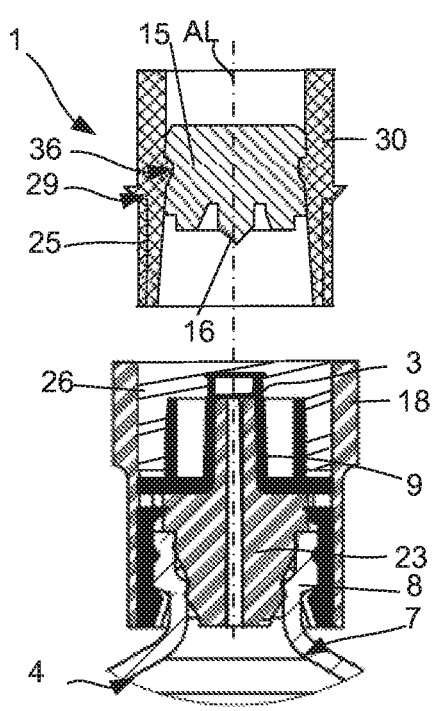
FIG. 1h shows in a view similar to FIG. 1f the components of the closure system after complete detachment of the closure element.

In order to allow a venting at the time of reconstituting or mixing the products or preparations contained in the dual-chamber container, wherein at the same time splashes are to be prevented, the closure element 15 is detachably connected in a force-fitting and/or form-fitting manner at least indirectly to a connection part, which here in a first variant takes the form of the securing ring 18. The connection is denoted by 22 and is achieved between the holding part 30, which holds the closure element 15, and the securing ring 18. The connection 22 is arranged and designed in such a way as to be suitable for permitting, once the securing part 19 has been separated from the securing ring 18 so as to cancel the form fit 31 acting in the direction of the longitudinal axis AL between the closure element 15 or the functional element carrying the latter, in this case the holding part 30, and the securing part 19, a relative movement between the closure element 15 and the applicator attachment 3 with a directional component in the direction of the longitudinal axis AL from the first functional position of the closure element (closed position) into at least one further functional position (splash-preventing and/or venting position), which is shown in FIG. 1g for the view according to FIG. 1e, while at least partially maintaining this connection 22, wherein in the at least one further functional position the pressure-tight, microbially tight and media-tight sealing of the through-opening 2 on the applicator attachment 3 by the closure element 15 is canceled so as to form an intermediate space 32 that is formed by the closure element 15 and the connection part, in this case also the holding part 30 which carries the closure element 15. This intermediate space 32 already permits a propagation of pressure therein. Medium exiting under pressure from the container 4 is collected in this intermediate space 32 and is not sprayed uncontrollably into the surrounding environment.

In one design, a relative movement within the connection 22 could already be sufficient, for example by minimal unscrewing of the closure element 15, so that spraying solution does not even enter the intermediate space 32 but rather "condenses" at the conical part of the closure element (sealing surface 16) and flows back into the channel of the closing stopper 42 that is formed by a through-opening 40.

In one particularly advantageous further development, venting means 21 are provided which are formed either by the connecting means or connecting elements forming the connection 22 on the closure element 15 or the holding part 30 carrying the latter and by a connection part, or else are incorporated in the connection 22 as separate channels.

The holding part 30 is designed as a hollow-cylindrical element which extends in the direction of the longitudinal axis AL and which comprises in a portion of the extension of its inner circumference 33 in the longitudinal direction connecting means 34 which can be operatively connected to complementary connecting means on a region of the outer circumference 37 of the closure element 15, so as to create a form-fitting connection 36. The closure element 15 is adapted in terms of its outer circumference 37 to the inner circumference 33 of the holding part 30. The holding part 30 designed as a hollow-cylindrical element may be designed with an invariable geometric shape and/or dimensions in the longitudinal direction in relation to the longitudinal axis AL or else with regions of different geometric shape and/or dimensions in the radial direction and/or longitudinal direction. In the case shown, the holding and carrying function is produced by means of a form fit through a latching connection, in that protrusions arranged on the inner circumference 33 engage in complementary recesses on the closure element 15. In one particularly advantageous design, the protrusions and recesses are designed to run around the entirety of the respective components in the circumferential direction, that is to say as a circumferential ring on the inner circumference 33 and a groove or channel on the outer circumference 37 of the closure element 15. Also conceivable is a design with cutouts and protrusions extending over a portion of the outer and inner circumference respectively, which cutouts and protrusions may in each case be arranged at an equal spacing from one another or else at a different spacing from one another. Also conceivable is the alternative configuration (not shown here) with radially oriented protrusions arranged on the outer circumference 37 of the closure element 15 and complementary cutouts on the inner circumference 33 of the holding part 30. The closure element 15 is arranged in the holding part 30 in such a way that the region having the sealing surface 16 is directed toward the applicator attachment 3 in the installed position. The sealing surface 16 is formed by a protrusion, in particular a sealing lip with a conical end region, which projects in the direction of the longitudinal axis AL on the side directed toward the applicator attachment 3.

In the case shown in FIGS. 1a to 1f, the connection 22 is designed as a screw connection with an integrated venting channel (not shown in detail here). In order to establish the connection 22, the holding part 30 carrying the closure element 15 comprises at least one external thread 25 which is arranged on a portion of its outer circumferential surface 31 with a directional component in the longitudinal direction and over a portion of the extension of the circumferential surface 24 in the longitudinal direction, which external thread engages with an internal thread 26 on a portion 27 extending in the direction of the longitudinal axis AL and forming an inner circumference, this portion being designed to run in the circumferential direction around the longitudinal axis AL on a connection part, here the securing ring 18. The venting channel is created for example by an interruption in the thread on the external thread 25 and/or internal thread 26, wherein preferably a channel which extends in the direction of the longitudinal axis AL is formed. The connecting means on the holding part 30, here the external thread 25, are arranged in the installed position here in the end region of the holding part 30 that is directed toward the applicator attachment 3.

A configuration (not shown here) in which the element 30 is designed in such a way that it has an internal thread and the securing ring 18 has an external thread would also be conceivable.

The closure securing function to ensure one single use under sterile conditions while avoiding an undesired opening and reclosing of the mouthpiece 8 (tamper-proof closure function) is achieved via the fact that the securing part 19 can be separated from the securing ring 18 with irreversible destruction of the connection and of the form fit 31 between the closure element 15 or, if the latter is integrated in the holding part 30, the holding part 30, said form fit acting in the longitudinal direction at least in the longitudinal direction directed away from the container 4 or the applicator attachment 3, said form fit being canceled when the securing part 19 is separated. The form fit 31 acting in the longitudinal direction is to this end arranged in the connection region 28 between the securing ring 18 and the securing part 19 and is achieved between the securing part 19 and the holding part 30. The holding part 30 carrying the closure element 15 has an annular elastic securing protrusion 29 which preferably runs entirely in the circumferential direction around the longitudinal axis AL on the circumferential surface 24 on the outer circumference of the holding part 30 in the installed position outside the portion having the external thread 25, which securing protrusion in the closed state of the applicator attachment 3 engages in the connection region 28 in the space in the shape of a ring segment, which is formed outside the connecting means 20, and a recess 38 in the area where the connecting means 20 are arranged, said connecting means forming for the securing protrusion 29 an undercut that acts in the direction of detachment of the closure element 15, counter thereto. The undercut formed by the recess 38 is shown in the detail view K in FIG. 1*f*. FIG. 1*e* shows the surface 39 of the securing part 19 which is directed toward the securing ring 18 and which is responsible for the form fit acting in the longitudinal direction counter to the direction of detachment of the closure element 15. The annular securing protrusion 29 is elastic and, with regard to a geometric design and dimensioning, is selected in such a way that, when the holding part 30 is screwed into the securing ring 18, the securing protrusion 29 bears under deformation against the outer circumference of the holding part 30 counter to the movement direction along the longitudinal axis AL and, when the closed position of the closure element 15 relative to the applicator attachment 3 is reached, the securing protrusion 29 engages in the annular space formed in the connection region 28 between the securing part 19 and the securing ring 18, unfolds in said annular space and comes to bear against the surface 39 directed from the securing part 19 in the longitudinal direction to the securing ring 18 or, if a slight relative movement is permitted, is oriented at a distance therefrom. In order now to unscrew the holding part 30 with the closure element 15 again, it is necessary to apply a force which destroys the connecting means 20 between the securing part 19 and the securing ring 18.

The elasticity of the annular securing protrusion 29 can be defined as a function of the material, the geometry and/or the dimensioning of the securing protrusion 29. In the case shown, as seen in cross section, the securing protrusion 29 is preferably designed with different dimensions in the longitudinal direction in the movement direction toward the applicator attachment 3, that is to say in the illustrated case in the screw-in direction. The securing protrusion 29 has the largest extension in the radial direction relative to the longitudinal axis AL in the radial direction, as seen in the direction of extension of the holding part 30, in the region pointing away from the connecting means for forming the connection 22. The securing protrusion 29 has the smallest extension relative to the longitudinal axis AL in the radial direction on its side directed toward the connection 22. Ideally, the circumferential securing protrusion 29 is characterized by a profile which tapers conically in the direction of the portion thereon that carries the connecting means, in particular the external thread 25.

The securing protrusion 29 may also be formed (not shown here) by ring segments. Configurations with individual elastic protrusions spaced apart in the circumferential direction around the holding part 30 are also conceivable.

In this embodiment, the applicator attachment 3 is advantageously formed by a safety cap 9 which can be placed onto and attached to the mouthpiece 8 as a separate component. The illustrated closure system 1 to this end comprises a closing stopper 23 which can be inserted into the opening 6 of the mouthpiece 8 in the end region 7 of the container 4 and is designed in such a way as to be suitable for bearing sealingly with a portion of its outer circumference against a portion of the inner circumference of the mouthpiece 8. The closing stopper 23 is further characterized by at least one through-opening 40 which forms a connecting channel and which extends through the closing stopper 23 in the installed position from a surface facing toward the container 4, as seen in the longitudinal direction, to its surface facing away from the container 4. In the connection region 42 to the container 4, the closing stopper 23 is adapted in terms of its shape and size to those of the opening 6 in the connection region on the container 4, here preferably as a rotationally symmetrical element with a circular cross section. The outer contour of the closing stopper 23, as seen in the circumferential direction, is preferably selected such that it can either be oversized and pressed into the opening 6 and/or is fixed in the mouthpiece 8 via a pressure-tight and media-tight form-fitting connection. In the case shown, the closing stopper 23 has on the outer circumference protrusions which run at least over a portion in the circumferential direction and which come to bear behind corresponding protrusions on the inner circumference of the mouthpiece 8. The closing stopper 23 furthermore has a collar 41 which forms a first container-side bearing surface for bearing against the container 4, in particular against the mouthpiece 8, and a second bearing surface directed away from the container 4 and thus formed on the applicator side, against which bearing surface the applicator attachment 3, here the safety cap 9 forming the latter, bears.

Besides the connection region 42 to the container 4, the closing stopper 23 comprises an end region 43 which is directed away therefrom in the direction of the longitudinal axis AL and which is adapted conically so as to match the inner contour of the through-opening 2 of the applicator attachment 3, extends into the space in the attachment region that is enclosed by the applicator attachment 3, and through which the connecting channel 40 is conducted into the attachment region so as to ensure a tight connection between the container interior and the applicator attachment 3. The closing stopper 23 may also be provided with a coating, as a result of which for example a barrier to leachables (extractable substances from the material) can be created. The applicator attachment 3 and the connection element 57 are formed by a functional element in the form of a safety cap 9 which serves to fix the closing stopper 23 relative to the container 4, in particular to the mouthpiece 8. The safety cap 9 is designed as a cylindrical element with different cross-sectional regions. It is characterized by two portions arranged one behind the other, a first portion 44 which forms the attachment region for the applicator and a second portion 45 which is also referred to as the connection region and performs the function of the connection element 57. In the case shown, the safety cap 9 is designed as a hollow-cylindrical element so as to form these two portions. The through-opening 2 is formed by the interior enclosed by the safety cap 9, or by a part of said interior. As seen in the installed position, the attachment region for the applicator is conical relative to the longitudinal axis AL, wherein the cone is designed to extend away from the container 4 along the longitudinal axis AL in the installed position. The second portion 45 in the form of the connection region is pot-shaped so as to surround the container 4 in the end region 7, in particular in the region of the mouthpiece 8. It forms at least one bearing surface, directed toward the container 4, for the closing stopper 23, which is suitable for fixing the latter relative to the mouthpiece 8 in the longitudinal direction. The bearing surface is in this case formed on the inner circumference of the portion 44 forming the connection region. Preferably, the bearing surfaces are surfaces directed toward the container 4 in the installed position.

Suitable means 46 are provided for fixing the safety cap 9 to the container 4. Said means comprise for example lamellae which are cut free on the safety cap 9 in the connection region and which extend in the direction of the container 4, said lamellae spreading open when placed onto the mouthpiece and being connected thereto via the closure securing unit 17, in particular the securing ring 18. Other designs are conceivable.

In the case shown, the safety cap 9 has a further annular collar 47 which is arranged coaxial with the portion 44 and runs around the latter and extends in the direction of the longitudinal axis AL. This collar is hollow-cylindrical. The collar 47 extends from the first portion in the direction of the longitudinal axis AL so as partially to surround the latter while maintaining a radial gap to the portion 44 forming the attachment region for the applicator. With regard to its dimensions selected in the radial direction, it may be designed so as to be suitable for forming a sealing pair with the holding part 30 in the closed position of the closure element 15.

As already mentioned, preferably all the components of the closure system 1 are designed substantially as rotationally symmetrical components in terms of their basic contour and are preferably arranged coaxially with respect to one another.

Figure 2E:
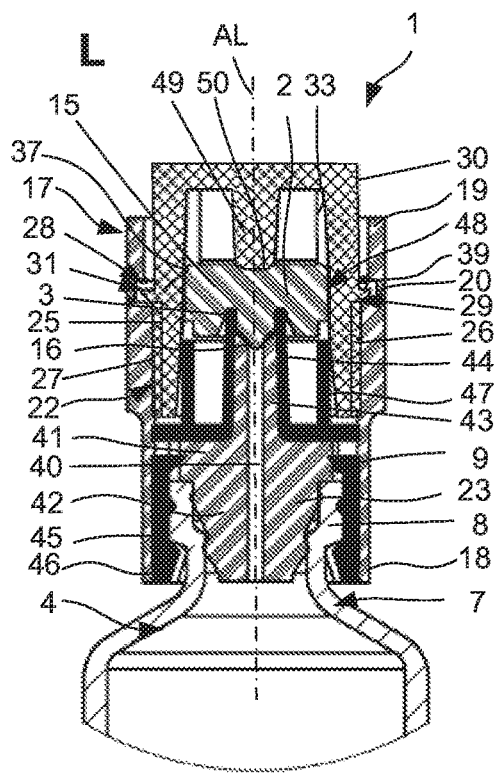
FIG. 2e shows a detail L in a view J-J from FIG. 2b.
Figure 2F:
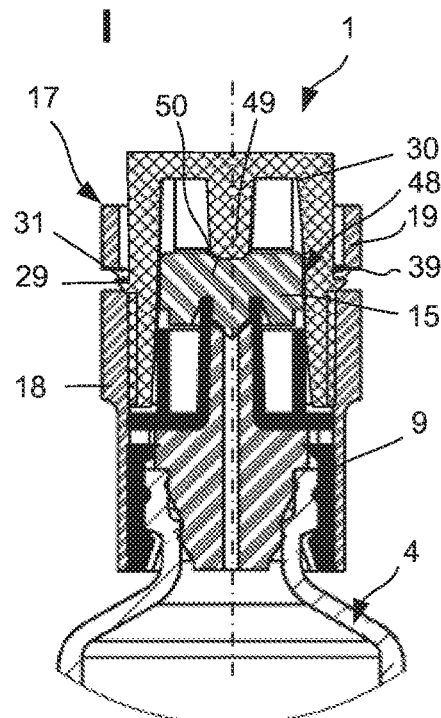
FIG. 2f shows a detail I in a view H-H from FIG. 2d.

FIGS. 2a to 2f show a further advantageous embodiment of a closure system 1 according to the invention in a further variant of a first design for an applicator attachment 3 in the form of a separate functional element which has a through-opening 2 and which is designed to be coupled to a container 4, based on the example of a syringe 5. The separate functional element forming the applicator attachment 3 is also designed here as a safety cap 9 and, besides forming the applicator attachment 3, serves to fix in position a closing stopper 23, which closes the opening of a container 4, in the direction of a longitudinal axis AL of the closure system 1, said longitudinal axis coinciding with the longitudinal axis of the container 4. In order to characterize the directional details, reference is made to a theoretical longitudinal axis AL which is oriented in the longitudinal direction and corresponds to the central axis of the components in the installed position. In the direction of the longitudinal axis AL means here in the longitudinal direction, and in the circumferential direction means around said longitudinal axis. FIG. 2b shows a syringe 5 in a first view, while FIG. 2d shows a further second view. FIG. 2a shows a section J-J according to FIG. 2b, and FIG. 2c shows a section H-H according to FIG. 2d. FIGS. 2e and 2f each show the closure system 1 with the applicator attachment 3 in section according to the details L and I from FIGS. 2a and 2c.

The basic structure and the basic function correspond to the embodiment shown in FIGS. 1a to 1f. The difference lies in how the connection between the holding part 30 and the closure element 15 is established. This is designed as a force-fitting connection 48 in the form of a press-fit connection. The closure element 15 is designed and dimensioned in such a way as to enter into a press fit with the inner circumference 33 on the holding part 30. To this end, in the simplest case, the outer circumference 37 is designed to be oversized in the circumferential direction relative to the inner circumference 33 of the holding part 30. In order to withstand the forces occurring in the "closed" functional state of the closure system 1 on the closure element 15 via the connection by the applicator attachment 3 to the container 4, preferably the holding part 30 is designed as a cap which is closed at one end, in which the closure element 15 comes to bear in the longitudinal direction against a stop surface 50 which is oriented counter to the detachment movement direction and which in the case shown comes to bear against a protrusion 49 which is arranged on the inner circumference of the closed end region of the holding part 30 at the end region directed away from the applicator device 3 and which extends in the longitudinal direction toward the closure element 15. The holding part 30 may in this case be cylindrical or, as in the case shown, slightly conical. The rest of the components, such as the closing stopper 23, the closure securing unit 17, in particular the securing ring 18 and the securing part 19, the connection 22 and the safety cap 9 and syringe 5 are designed in manner analogous to the design described in FIGS. 1a to 1h, for which reason full reference is made thereto.

Figure 3A:
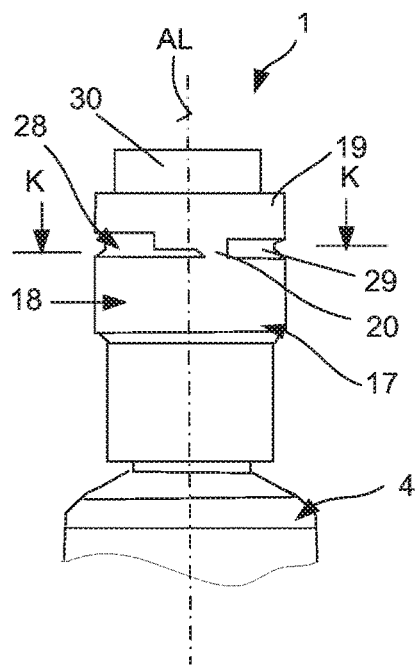
FIG. 3a shows the closure system in a view similar to FIG. 1c.

FIG. 3a shows the closure system 1 in a view according to FIG. 1c. It is possible to see here the connecting means 20 which comprise at least one web that extends in the direction of the longitudinal axis AL and is articulated on or fixedly connected to the securing part 19 and the securing ring 18 by its end regions pointing away from one another. The web may in this case be configured with a varying cross section in the longitudinal direction toward the securing ring 18 or (in a manner not shown here) toward the securing part 19. A change in cross section in the region extending in the longitudinal direction in a direction transverse to the longitudinal axis AL is also conceivable.

Figure 3B:
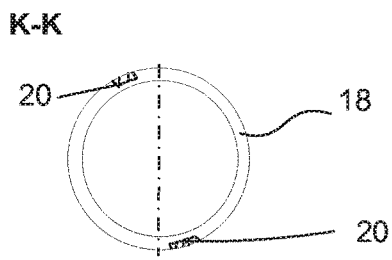

In the case shown, it is possible to see one connecting means 20. A configuration with two or more connecting means 20 arranged at a distance from one another in the circumferential direction around the longitudinal axis AL is also conceivable for example. FIG. 3b shows by way of example, based on a sectional view K-K according to FIG. 3a, a design with two such connecting means 20 which are arranged at a distance from one another in the circumferential direction and which keep the securing ring 18 and the securing part 19 at a distance from one another in the regions free from connecting means 20. A view in section through the connecting means 20 on a surface formed at the end region of the securing ring 18 pointing toward the securing part 19 is shown. It can be seen that the connecting means 20 do not extend over the entire extension of the connection surfaces on the parts—securing ring 18 and securing part 19—that form the closure securing unit 17, but rather in an analogous design (not shown here) form on the securing part 19 an undercut for a securing protrusion 29 in the form of a circumferential elastic ring or a ring formed of ring segments that is formed on the closure element 15 or holding part 30.

Figure 4:
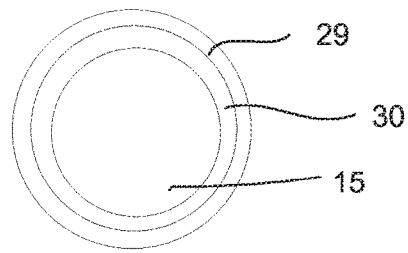
FIG. 4 shows a plan view of the holding part.

FIG. 4 shows, in a plan view of a holding part 30 according to FIG. 1g, the design with a securing protrusion 29 running around the holding part 30 in the circumferential direction. Said securing protrusion is designed in such a way that, in the first functional position of the closure element 15 in the "closed" functional state, it engages in the intermediate space formed between the securing part 19 and the securing ring 18, in particular the mutually facing surfaces thereof, within the extension of the connection region 28.

In an alternative design which is not shown here, the securing protrusion 29 may also have in portions protrusions which come to lie directly behind the connecting means 20 comprising at least one web or webs, and which cut the connecting means 20, in particular the webs, when the holding part 30 is screwed on.

FIG. 5a shows by way of example, based on a view according to FIG. 1e, a further design of a connection which permits a relative movement, as a form-fitting connection 51 between the closure element 15 or the holding part 30 carrying the latter and a connection part, here once again in the form of the securing ring 18. The basic structure—apart from the connection between the connection part in the form of the securing ring 18 and the holding part 30—is analogous to the design described in FIGS. 1a to 1h, for which reason reference is made thereto.

The connection 51 is designed as a form-fitting connection via protrusions 53 which are arranged on the outer circumference of the holding part 30 and which engage in recesses 52 provided for this purpose on the securing ring 18. The form fit, as seen in the longitudinal direction, is formed here by the configuration of the recesses 52 with a first open-edged portion extending in the longitudinal direction and an adjoining further portion which extends in the circumferential direction, wherein the form-fitting elements in the form of the protrusions 53 engage in these recesses 52 and, upon assembly, are guided therein in the first functional position of the closure element. The second functional position (splash-preventing and/or venting position), which is not shown here, is achieved by rotating the closure element 15, wherein the protrusions 53 are latched into latching positions 56 in the recesses 52, said latching positions being provided for this purpose along the recesses 52. In order to apply the product, the protrusions 53 of the closure element are moved out of these latching positions 56 and, by moving the protrusions 53 out of the recesses 52, the closure element 15 is separated completely from the applicator attachment 3.

FIG. 5b shows by way of example a possible design of a guide formed by the recesses 52 for the protrusions 53 on the holding part 30, according to the design in FIG. 5a. The recesses extend here in the direction of the longitudinal axis from the end region of the securing ring 18 that faces toward the securing part 19 in the installed position, so as to create a connection region in the longitudinal direction of the closure system 1 which permits a relative movement between the closure element 15 or holding part 30 and the connection part in the form of the securing ring 18. It is possible to see here the first portion running in the longitudinal direction and the second portion extending in the circumferential direction. Here, the second portion forms the connection region, which permits a form fit in the longitudinal direction. The first portion serves for the relative movement.

If the profile of the recess and thus of the connection region is clearly subdivided here into a portion acting in the longitudinal and circumferential direction, it is likewise conceivable also to form the first portion so that it runs at least with one directional component in the circumferential direction.

In one advantageous further development, a latching position 56 is provided in the guide-forming recess 52. In this regard, FIGS. 5d1 and 5d2 show two possible designs of the recess 52 based on a detail from the portion of the securing ring 18 that forms the connection region. The latching position 56 is formed in both cases on the portion of the recess 52 that is oriented in the circumferential direction, wherein according to FIG. 5d1 it is formed at a distance from the vertically oriented region, whereas FIG. 5d2 shows a possibility in which the latching position 56 is formed in the form of a recess which is open at the edge next to the vertically oriented portion of the recess 52.

FIG. 5c shows the protrusions 53 on the holding part 30. Said protrusions are arranged and designed in such a way as to be suitable for engaging in the recesses 52 on the securing part 18. The arrangement on the outer circumference of the holding part 30 takes place as a function of the position of the holding part 30 in the closed position of the closure element 15 and of the arrangement of the recess 52 that is required in order to achieve the form fit, in particular of the portion of said recess that is oriented in the circumferential direction.

In the installed position, the protrusions 53 are moreover arranged in the closure system 1 in the end region directed toward the applicator attachment 3.

FIG. 6 shows by way of example a closure system 1 according to the invention in a second design with a direct connection between the closure element 15 and the connection part, in particular the securing ring 18, in an axial section analogous to the designs according to FIGS. 1 and 2. The basic structure of the closing stopper 23, the safety cap 9 free of a portion 47, the closure securing unit 47, the securing ring 18, the securing part 19, the connecting element 20 and the form fit 31 corresponds to what has been described in the aforementioned figures, for which region reference is simply made thereto. The connection 22 which permits a relative movement is formed here directly between the closure element 15 and the connection part in the form of the securing ring 18. The connecting means which are necessary for this and which can be operatively connected to one another are arranged on the outer circumference of the closure element 15 and on the inner circumference of the securing ring 18. In the case shown, this is configured for example as a screw connection which is shown in the closed position of the closure element 15 relative to the applicator attachment 3. The closure element 15 to this end has on the outer circumference an external thread 54 which can be brought into engagement with an internal thread 26 on the securing ring 18.

In contrast, FIG. 7 shows in an axial section a closure system 1 according to the invention in a second design with a direct connection between the closure element 15 and the connection part, here for example in the form of a safety cap 9 forming the applicator attachment 3.

In order to achieve the connection between the closure element 15 and the applicator attachment 3, in particular the safety cap 9, the latter has a further portion 47 which, in a manner analogous to the design shown in FIGS. 1a to 1h, is configured as a collar which runs annularly and extends in the longitudinal direction, said collar being designed and arranged so as to be suitable for carrying connecting means for achieving a connection 22 between the closure element 15 and the safety cap 9 which permits a relative movement in the longitudinal direction, which connecting means can be operatively connected to complementary connecting means on the closure element 15. In the design shown in FIG. 7, the connection 22 which permits a relative movement is configured as a force-fitting connection in the form of a screw connection, for which purpose the closure element has, on a portion of its outer circumference running in the circumferential direction, an external thread which can be brought into engagement with an internal thread arranged on the safety cap 9, in particular the portion 47.

FIGS. 8a and 8b serve to illustrate an alternative allocation, relative to the design in FIG. 7, of the external and internal thread to the components safety cap 9 and closure element 15. In this case, the closure element 15 is designed with a portion having an internal thread, while the safety cap 9, particularly in the portion 47, is designed with a region having an external thread.

In the designs shown in FIGS. 6 to 8, the form fit 31 which is formed at least indirectly between the closure element 15 and the securing part 19 and which acts in the direction of the longitudinal axis AL is produced in a manner analogous to the designs of FIGS. 1 to 3, but in contrast thereto the securing protrusion 29 is arranged directly on the closure element 15, in particular on the outer circumference 37, in a manner extending around said closure element in the circumferential direction. For this, what has been stated above in relation to the securing protrusion on the holding part 30 applies.

FIG. 9a shows, based on a sectional view, an embodiment according to FIG. 7 with an alternative design of the connection between the securing ring 18 and the securing part 19. The securing part 19 is designed as a securing cap 19 and encloses at least a portion of the applicator attachment 3 as well as the closure element 15. An advantageous design of the closure securing unit 17 is shown by way of example in FIG. 9b. The securing cap 19 and the securing ring 18 form an annular gap between them and are connected to one another via a plurality of connecting webs 59 and 60. The latter may be arranged in an alternating manner or in another selected arrangement relative to one another in the circumferential direction, wherein the number of connecting webs 59 and 60 may differ from one another. In the case shown, the connecting webs 59 provided for separating the connection and for forming a predetermined breaking point are designed with a cross section which tapers in the direction of the securing ring 18, while the pressure-absorbing webs are designed with a cross section which tapers from the securing ring 18 to the securing cap. Here, the securing cap surrounds the closure element 15 in the circumferential direction over a substantial part of the extension thereof and of the extension of the connection 22 as seen in the longitudinal direction of the container 4.

Other designs (not shown here) are conceivable. For instance, the connecting means may also comprise connecting webs which connect the securing cap to the securing ring 18, which connecting webs compensate a force that is exerted by the lyophilizer plate and that acts vertically on the closure securing unit 17 so as to fully close the container 4 without breakage. To this end, a spacer part for absorbing pressure may optionally be provided between in each case two adjacent connecting webs, said spacer part being fixedly connected to the securing cap and the free end of said spacer part being located opposite, and at a small distance from, the securing ring 18. The reverse allocation is also conceivable.

The connecting webs at the same time form a predetermined breaking point which makes it possible, at the time of desired use, in particular at the time of connecting the appropriate applicator to the container 4, to easily break open the latter.

FIG. 10 shows by way of example, based on a view according to FIG. 2f, the first assembled position of the closure system 1 relative to the container 4 and the positioning of the individual components of the closure system 1 relative to one another in this assembled position, as may be assumed in one particularly advantageous application in a lyophilizer during the lyophilization. The closure system 1 has been preassembled as a unit and has preferably already been sterilized.

The closure system 1 is arranged coaxial with the longitudinal axis and is characterized by a positioning of the individual components of the closure system 1 relative to one another in such a way as to permit a connection of the opening 6 of the container 4 to the surrounding environment. In this first assembled position, there is a connection between the opening 6 and the surrounding environment, that is to say the opening 6 on the container 4 is not sealingly closed. In this assembled position, the closure element 15 is free of a sealing arrangement of the applicator attachment 3. This is achieved by the positioning of the closure element 15 relative to the closure securing unit 17 in the preassembled closure system 1 and the positioning of the closure securing unit 17 relative to the connection element 57. As seen in the longitudinal direction, in this position the closure securing unit 17 is positioned relative to the connection element 57 in such a way that it surrounds the connection element 57 only over a portion of its extension in the longitudinal direction, that is to say is not fully pushed onto the connection element 57. The end region of the closure securing unit 17 which in the installed position is subsequently on the container side is positioned relative to the connection element 57 by means of positioning aids on the inner circumference of the securing ring 18 of the closure securing unit 17 and/or on the outer circumference of the connection element 57. In the simplest case, these positioning aids are designed as protrusions which cooperate in a force-fitting manner with the counter-face on the respective other element or in a form-fitting manner with complementary means.

The positioning of the connection element 57 relative to the container 4, in particular relative to the opening 6 in the end region 7, takes place in the first assembled position in a first position on the end region 7 of the container 4. In the case shown, this first position is achieved by the cooperation of the means 46 on the connection element 57 and corresponding complementary protrusions and/or recesses which are suitable for cooperating therewith and which are provided on the end region 7 of the container 4, this first position being denoted 61. In this position, the opening 6 is thus not closed by the closing stopper 23. In a design of the closure system 1 according to FIG. 2f and in all the designs in which the connection element 57 for fixing the closure system 1 to the container 4 is formed by a safety cap 9 forming the applicator attachment 3, the safety cap 9 in the first assembled position is arranged offset relative to the container 4 in the longitudinal direction in comparison to the actual closed position. The position of the applicator attachment 3 formed thereon relative to the container 4 in the longitudinal direction thus also changes. A gap between the opening of the applicator attachment 3 and the closure element 15 which permits a connection to the surrounding environment is achieved by the positioning of the closure securing unit 17 relative to the safety cap 9.

The first assembled position of the closure system 1 on the container 4 is thus characterized by a first position, preferably a first latching position, of the connection element 57 on the container 4 and a predefined position of the closure securing unit 17 and of the closure element 15 coupled thereto in the longitudinal direction relative to the connection element 57.

The means 46 which are provided on the end region facing away from the applicator attachment 3 serve here in collaboration with complementary means on the container to fix the components in position in this first assembled position.

In this first assembled position, relative to the connection element 57, in particular the safety cap 9, the closure securing unit 17 is arranged in a position differing from the closed position, said position being characterized by a position of the closure element 15 relative to the applicator attachment 3 that is free of a sealing closure. This position is characterized by the offset position of the closure securing unit 17 relative to the connection element 57, in comparison to the closed position as seen in the longitudinal direction of the closure system 1.

The closure securing unit 17, in particular the securing ring and also the closure element 15 coupled thereto, are thus displaced relative to the container 4, in particular the connection element 57, in the longitudinal direction of the closure system 1. For this, a latching position for the closure securing unit 17 may preferably be provided on the connection element 57, which latching position may be created for example via form-fitting elements or may result from the design of the connection element 57 and the securing ring 18. In the first assembled position, vapors arising during the lyophilization can thus be dissipated.

The closure securing unit 17 is then displaced toward the container 4 in the longitudinal direction, wherein a relative movement of the closure securing unit 17 relative to the safety cap 9 and thus the connection element 57 takes place, during which the closure element 15 seals the applicator attachment 3 and at the same time the safety cap 9 and thus the connection element 57 are moved into the final closed position, referred to as the second assembled position, as shown in FIG. 2f. It will be understood that intermediate positions may also be possible between the first and second assembled position.

In the design shown in FIG. 2f and FIG. 10, the fixing of the closure system 1 to the container 4 takes place via the configuration of the connection element 57, in particular the container-side end region of the safety cap 9 and the dimensioning and configuration of the end region of the securing ring 18 facing toward the container 4. Preferably, the connection element 57 is tensioned relative to the container 4 by the end region of the securing ring 18. In order to be able to generate a sufficiently high surface pressure, a given size of the surface areas of the securing ring 18 and connection element 57 that are to be operatively connected must be provided in the longitudinal direction of the closure system 1.

FIGS. 11a and 11b show a particularly advantageous further development with a tensioning ring 58 for tensioning the securing ring 18 to the connection element 57 or the container 4, as a result of which a particular short construction can be achieved for the closure system 1 in the longitudinal direction and thus also in collaboration with a container 4.

FIG. 11a shows the further development of a closure system 1 based on the example of the closure system 1 described in FIG. 2 in a view according to FIG. 2f in collaboration with the container 4 in its second assembled position, which is characterized by the tight closure of the container 4. The basic structure and the basic function of the closure system 1 correspond to the designs shown in FIG. 2, apart from the application of the fixing force for fixing the closure system 1 to the container 4. With regard to the basic design and functioning, reference is therefore made to what has been stated in relation to said figures. Identical reference signs are used for identical elements. Furthermore the closure system 1—apart from the distinguishing feature of the tensioning by a separate tensioning ring 58 which characterizes this embodiment—may also be designed (not shown here) in a manner analogous to the other described embodiments.

In the case shown, the force necessary for fixing the connection element 57 relative to the container 4 is applied by a tensioning ring 58. In the closed position, the latter engages fully around the securing ring 18 in the circumferential direction. The use of a clamping ring which only partially surrounds the securing ring 18 in the circumferential direction would also be conceivable. Since the tensioning need no longer be generated solely via the dimensioning of the securing ring 18, the latter may be shortened in terms of its extension in the longitudinal direction. This thus also applies to the connection element 57 and, if the latter is formed on the safety cap 9, also to said safety cap.

FIG. 11b shows, in a manner analogous to FIG. 10, the closure system in the first assembled position with the separate tensioning ring, the assembly direction thereof being indicated by an arrow. However, the tensioning ring 58 is pushed onto the closure system 1 only once the latter is already in the second assembled position relative to the container. This may take place while still in a lyophilizer or else after removal from the latter.

FIGS. 1 to 8 show embodiments with an applicator attachment 3 which is formed by a safety cap 9. FIG. 13a shows by way of example an alternative embodiment of the applicator attachment 3 by the closing stopper 23. For this embodiment, the closing stopper 23 is designed and arranged in such a way as to be suitable, besides forming a sealing surface which runs in the circumferential direction on the outer circumference, also for establishing the form-fitting and/or force-fitting connection to the mouthpiece 8. This is achieved by suitable shaping, for example in that the closing stopper 23 has a portion 23a which is suitable for bearing, at least over a portion, sealingly against the inner circumference of the mouthpiece 8 and also a further portion 23b which is designed to engage around the mouthpiece 8 perpendicular to the longitudinal axis AL. The connection region is formed by a further portion 23c which surrounds the connection region annularly at a distance therefrom. The means for achieving the connection 22 to the closure element 15 may in this case be arranged on the inner or outer circumference of the portion 23c, depending on the design of the complementary means on the closure element. Besides this configuration, a further possibility lies in forming a thread on the container 4. The closing stopper 23 need only be screwed onto or screwed into this region.

FIG. 13b shows a design with the applicator attachment 3 formed by shaping on the container 4. In order to fix the closure system 1, a retaining ring 55 is pushed onto the latter and is fastened thereto in a form-fitting and/or force-fitting manner.

FIG. 12a shows by way of example, in a schematic simplified diagram, the sequence of a method for producing a syringe 5. In a first method step VA, the closure system 1 is preassembled. In method step VB, the entire closure system 1 is sterilized and in method step VC is supplemented by a suitably designed container 4 with a piston 11 so as to form the syringe 5. In VC1, the closure system is preferably positioned relative to the container in such a way that the safety cap 9 engages around the mouthpiece 8 and the closing stopper is arranged in the opening 6. The closure securing unit 17 is in the first assembled position. In this position, the closure element 15 is away from the sealing position relative to the applicator attachment 3. In this position, the lyophilization takes place in VC2, while in VC3 the closure securing unit 17 is moved relative to the connection element 57 into the second assembled position by a vertical movement and in this position the connection element 57 is fixed relative to the container 4 and thus to the applicator attachment 3 and the closure element 15 is moved into a position sealing the applicator attachment 3.

FIG. 12b shows by way of example, in a schematic simplified diagram, the sequence of a method for opening the closure system 1 again. In method step VD, the closure system 1 is in the "closed" functional state. The applicator attachment 3 is closed by the closure element 15 in a pressure-tight, media-tight and microbially tight manner. In method step VE, the connection between the securing part 19 and the securing ring 18 is separated, thereby releasing the form fit 31 acting in the longitudinal direction between the closure element 15 or the holding part 30 holding the latter and the securing part 19. The separation may be initiated by triggering the relative movement between the closure element 15 or holding part 30 and the connection part. In VF, the closure element 15 is moved into the second functional position, which ensures splash prevention and venting. To this end, the closure element 15 or the holding part 30 is moved within the connection according to the necessary movement direction and is brought into this functional position. Once venting has taken place, the closure element can be fully moved away from the applicator attachment 3 in VG, and in VH an applicator can be connected to the applicator attachment 3.

The invention claimed is:

1. A closure system (1) for an applicator attachment (3) on a container (4) for pharmaceutical preparations, said applicator attachment extending along a theoretical longitudinal axis (AL), having a through-opening (2) and being designed for the connection of an applicator, said closure system comprising a closure element (15) with at least one region having a sealing surface (16) for sealing the through-opening (2) of the applicator attachment (3);

a sleeve-like connection element (57) for force-fitting and/or form-fitting connection to the container (4) at an end region thereof;

a closure securing unit (17) arranged coaxial with the connection element (57) and surrounding the latter in the circumferential direction, said closure securing unit comprising a securing ring (18) and a securing part (19) which is connected to the securing ring (18) via connecting means (20) so as to be separable with irreversible destruction of the latter, wherein the closure securing unit (17) is designed to surround at least the end region of the applicator attachment (3) and the closure element (15) in the circumferential direction around the longitudinal axis (AL) over a portion of the extension in the longitudinal direction and to fix the sleeve-like connection element (57) to the container (4) by a relative movement in the longitudinal direction relative to the connection element (57) from a first into a second assembled position; wherein;

the closure element (15) is detachably connected in a force-fitting and/or form-fitting manner at least indirectly to a connection part formed by the applicator attachment (3) or a by a functional element carrying the latter or by the securing ring (18), wherein the closure element (15) in a first functional position defined as the closed position closes the through-opening (2) on the applicator attachment (3) in a pressure-tight, media-tight and microbially tight manner, and the form-fitting and/or force-fitting connection (22, 51) is arranged and designed in such a way as to be suitable for permitting, after the securing part (19) has been separated from the securing ring (18), a relative movement between the components involved in the connection (22, 51), in particular the closure element (15) and the connection part, with a directional component in the direction of the longitudinal axis (AL) from the first functional position (closed position) into at least one further functional position (splash-preventing and/or venting position) while at least partially maintaining this connection (22, 51), wherein in the at least one further functional position the pressure-tight, media-tight and microbially tight sealing of the through-opening (2) on the applicator attachment (3) by the closure element is canceled so as to form an intermediate space (32) that is formed between the closure element (15), the applicator attachment (3) and/or the connection part;

the closure system further comprises venting means (21) are provided, which are integrated at least partially in the at least indirect connection (22, 51) between the closure element (15) and the connection part and are arranged and designed in such a way as to be suitable for connecting the through-opening (2) on the applicator attachment (3) to the surrounding environment at least in the second functional position of the closure element (15); and in order to establish the connection (22) the holding part (30) carrying the closure element (15) comprises at least one external thread (25) which is arranged on a portion of its outer circumferential surface (31) with a directional component in the longitudinal direction and over a portion of the extension of the circumferential surface (24) in the longitudinal direction, which external thread engages with an internal thread (26) on a portion (27) extending in the direction of the longitudinal axis (AL) and forming an inner circumference, wherein the portion being designed to run in the circumferential direction around the longitudinal axis (AL) on a connection part and a venting channel as venting means is created by an interruption in the thread on the external thread (25) and/or internal thread (26), wherein said renting channel extends in the direction of the longitudinal axis (AL).

2. The closure system (1) according to claim 1, wherein the at least indirect connection (22, 51) between the closure element (15) and the connection part is formed indirectly by a connection between a holding part (30), which surrounds the closure element (15) as seen at least in the circumferential direction around the longitudinal axis (AL) and is connected thereto, and the connection part, and the connection between the closure element (15) and the holding part (30) is designed as one of the connections mentioned below or as a combination of these:

force-fitting connection
form-fitting connection
material bond
and
the form fit (31) which acts in the direction of the longitudinal axis (AL) and which is formed at least indirectly between the closure element (15) and the securing part (19) is formed between the holding part (30) and the securing part (19).

3. The closure system (1) according to claim 1, wherein the at least indirect connection (22, 51) between the closure element (15) and the connection part is formed by a direct connection of the closure element (15) and the connection part, and the form fit (31) which acts in the direction of the longitudinal axis (AL) and which is formed at least indirectly between the closure element (15) and the securing part (19) is formed between the closure element (15) and the securing part (19).

4. The closure system (1) according to claim 1, wherein the at least indirect connection (22, 51) which permits a relative movement between the closure element (15) and the connection element with a directional component in the direction of the longitudinal axis (AL) is designed at least over a portion with a form-fitting and/or force-fitting connection acting in the direction of the longitudinal axis (AL) counter to the detachment movement direction of the closure element (15).

5. The closure system (1) according to claim 1, wherein the at least indirect connection (22, 51) which permits a relative movement between the closure element (15) and the connection element with a directional component in the direction of the longitudinal axis (AL) is formed by a screw connection, comprising a portion with an internal thread on one of the components to be connected to one another—closure element (15)/holding part (30) or connection part—and a portion with an external thread on the respective other of the components to be connected to one another—connection part or closure element (15)/holding part (30).

6. The closure system (1) according to claim 5, wherein at least one venting channel is provided which extends with at least a main directional component parallel to the longitudinal axis (AL) and which is incorporated in the thread or is formed by interrupting the thread turns so as to form thread-free regions on at least one of the components to be connected to one another—closure element (15)/holding part (30) or connection part—wherein the thread-free regions are arranged and dimensioned in such a way that the sum of the thread-free angle regions is in the range from 5° to 90°, preferably 8° to 60°, particularly preferably 10° to 45°, relative to the full circumference 360°.

7. The closure system (1) according to claim 5, wherein the further functional position (venting position) between the closure element (15) and the connection element is defined as a function of the geometry and/or dimensioning of the thread, in particular the thread pitch.

8. The closure system (1) according to claim 1, wherein the at least indirect connection (22, 51) which permits a relative movement between the closure element (15) and the connection element with a directional component in the direction of the longitudinal axis (AL) is designed as a form-fitting connection, comprising protrusions which are arranged on one of the components to be connected—closure element (15)/holding part (30) or connection part—and which point in the direction of the other component, which protrusions can be introduced into open-edged cutouts (52) which run in the direction of the longitudinal axis on the respective other of the components to be connected to one another—connection part or closure element (15)/holding part (30)—and which open in each case in a portion oriented in the circumferential direction.

9. The closure system (1) according to claim 1, wherein in the first functional position between the closure element (15) and the securing part (19) a form fit (31) is provided which acts at least in one direction in the direction of the longitudinal axis (AL), and the form fit (31) which acts in the direction of the longitudinal axis (AL) and which is formed at least indirectly between the closure element (15) and the securing part (19) is arranged and designed in the connection region (28) between the securing part (19) and the securing ring (18) in such a way that the form fit is canceled when the securing part (19) is separated.

10. The closure system (1) according to claim 9, wherein the securing part (19) and the securing ring (18) are connected to one another via at least one connecting means (20) formed in the longitudinal direction, and the securing part (19) has a surface (39) which points toward the securing ring (18) and which in the first functional position of the closure element (15) acts as a stop surface in the longitudinal direction for at least one elastic securing protrusion (29) which is at least in the shape of a ring segment and which is formed on the closure element (15) or on the holding part (30) so as to be arranged around the latter in the circumferential direction.

11. The closure system (1) according to claim 1, wherein the connection element (57) has means (46) for coupling it to the container (4) in a form-fitting and/or force-fitting manner.

12. The closure system (1) according to claim 1, wherein the applicator attachment (3) is hollow-cylindrical and has at least one conical portion, wherein the applicator attachment (3) is formed by a region integrally formed on the container (4) and the securing ring (18) is fastened to the container (4) in the circumferential direction and in the direction of the longitudinal axis (AL) directly or via a retaining ring which surrounds the applicator attachment (3) in the circumferential direction.

13. The closure system (1) according to claim 1, wherein the applicator attachment (3) is hollow-cylindrical and has at least one conical portion, and the applicator attachment (3) is formed by a separate element or is integrally formed on a component of the closure system (1) which is connected at least indirectly to the container (4) in a form-fitting and/or force-fitting manner.

14. The closure system (1) according to claim 13, wherein the closure system (1) comprises a closing stopper (23) which can be inserted into an end opening (6) on the container (4), has a through-opening (40) for connecting between the container interior and the surrounding environment and has an outer circumferential surface which runs relative to the longitudinal axis (AL) and which forms over a portion a sealing surface for bearing against a portion of the inner circumference of the container (4) in the region of the end opening (6),
the closing stopper is fixed to the container (4) in a force-fitting and/or form-fitting manner via a safety cap (9) which encloses said closing stopper, and
the applicator attachment (3) is formed by at least a portion of the safety cap (9) or a portion on the closing stopper (23) that extends through the safety cap (9).

15. The closure system (1) according to claim 14, wherein the safety cap (9) is designed as a hollow-cylindrical element, comprising at least two portions arranged coaxial with one another, a first portion (44) for forming the connection region of the applicator attachment (3), a second portion (45)

for attachment to the container (4), and optionally a third portion (47) for the arrangement of connecting means for the indirect force-fitting and/or form-fitting connection (22, 51) of the closure element (15) to a connection part when the safety cap (9) is designed as the connection part, wherein the optionally provided third portion surrounds the first portion in the circumferential direction at least partially over the extension thereof in the direction of the longitudinal axis (AL) so as to form an intermediate space.

16. The closure system (1) according to claim 14, wherein the connection element (57) is formed by the safety cap (9), which in the region of connection to the container (4) has latching means which act on the latter.

17. The closure system (1) according to claim 1, wherein the closure securing unit (17) is designed to fix the sleeve-like connection element (57) to the container (4) at least partially during a relative movement in the longitudinal direction relative to the connection element (57) from a first into a second assembled position.

18. The closure system (1) according to claim 17, wherein a tensioning ring (58) is provided which in the second assembled position surrounds the securing ring (18) of the closure securing device (17) in the circumferential direction in the extension region of the connection element (57) and which tensions the securing ring and the connection element (57) relative to the container (4).

19. The closure system (1) according to claim 1, wherein, together with the applicator attachment (3), the closure system (1) is designed as a preassembled unit which maintains the closed position between the closure element (15) and the applicator attachment (3).

20. A container (4) for holding pharmaceutical preparations, comprising an applicator attachment (3) which is formed thereon or can be attached thereto and which has a closure system (1) according to claim 1.

21. The container (4) according to claim 20, wherein the container (4) is designed as a dual-chamber container with a mouthpiece (8) for forming the opening (6) and for the connection of the applicator attachment (3), wherein the mouthpiece (8) comprises at least two means, configured in a manner complementary to the means (46) on the connection element (57), for establishing a force and/or form fit, said means being offset relative to one another in the longitudinal direction in order to keep the connection element (57) in a first position relative to the container (4) in the first assembled position of the closure system (1) and in order to fix the connection element (57) in a second position relative to the container (4) in the second assembled position of the closure system (1).

22. A syringe (5) for medical purposes, comprising a container (4) according to claim 20.

* * * * *